United States Patent
Erazo-Majewicz et al.

(10) Patent No.: US 7,589,051 B2
(45) Date of Patent: Sep. 15, 2009

(54) CATIONIC, OXIDIZED POLYSACCHARIDES IN CONDITIONING APPLICATIONS

(75) Inventors: Paquita Erazo-Majewicz, Newark, DE (US); Jashawant J. Modi, Hockessin, DE (US); Zu-Feng Xu, Newark, DE (US)

(73) Assignee: Hercules Incorporated, Wilmington, DE (US)

( * ) Notice: Subject to any disclaimer, the term of this patent is extended or adjusted under 35 U.S.C. 154(b) by 168 days.

(21) Appl. No.: 10/821,013

(22) Filed: Apr. 8, 2004

(65) Prior Publication Data

US 2005/0227902 A1 Oct. 13, 2005

(51) Int. Cl.
*A61K 8/73* (2006.01)
*C08B 15/06* (2006.01)
*C11D 3/22* (2006.01)
*C11D 3/37* (2006.01)

(52) U.S. Cl. .................. 510/121; 510/119; 510/124; 510/151; 510/330; 510/470; 510/473; 510/504; 424/401; 424/479; 424/480; 424/70.13; 514/54

(58) Field of Classification Search .............. 510/119, 510/121, 124, 151, 330, 470, 473, 504; 424/401, 424/479, 480, 70.13; 514/54
See application file for complete search history.

(56) References Cited

U.S. PATENT DOCUMENTS

| 5,480,984 A | 1/1996 | Angerer et al. ............ 536/88 |
| 5,489,674 A | 2/1996 | Yeh ............................ 356/114 |
| 5,756,720 A | 5/1998 | Chowdhary .................. 536/124 |
| 6,054,511 A | 4/2000 | Angerer et al. .............. 524/42 |
| 6,210,689 B1 | 4/2001 | Martino et al. .............. 424/401 |
| 2003/0199403 A1 | 10/2003 | Wells et al. .................. 510/119 |
| 2003/0211952 A1* | 11/2003 | Erazo-Majewicz et al. .. 510/119 |

FOREIGN PATENT DOCUMENTS

| EP | WO 03/095497 | * 11/2003 |
| JP | 10-36403 | 2/1998 |
| WO | 99/36054 A1 | 7/1999 |
| WO | WO 02/12349 A2 | 2/2002 |
| WO | WO 03/095497 A1 | 11/2003 |

OTHER PUBLICATIONS

Conditioning Agents for Hair and Skin. Ed. R. Schueller and P. Romanowski. Marcel Dekker, Inc. Ny, NY (1999).
Hair Conditioning Polymer/Surfactant Complexes: Structure and Efficacy. V. Andre, R. Norenberg, J. Rieger and P. Hossel. Proceedings, XXIst IFSCC International Congress 2000. Berlin, p. 189-199.
Hair Conditioning Polymer/Surfactant Complexes: Structure and Efficacy. V. Andre, R. Norenberg, J. Rieger and P. Hossel. Proceedings, XXIst IFSCC International Congress 2000. Berlin, p. 189-199, 2000.
Cationic Conditioners That Revitalize Hair and Skin. Amerchol Product Literature. WSP801 (Jul. 1998).

* cited by examiner

*Primary Examiner*—Brian P Mruk
(74) *Attorney, Agent, or Firm*—Robert O'Flynn O'Brien; Joanne Mary Fobare Rossi

(57) ABSTRACT

A cationic, oxidized polysaccharide or derivative thereof that has a mean average molecular weight (Mw) having a lower limit of 50,000 and an upper limit of 1,000,000 and an aldehyde functionality content of at least 0.001 meq/gram is used in personal care and household care compositions. This cationic, oxidized polysaccharide is prepared in continuous or batch processes using hydrolytic reagents, oxidizing reagents, or combination of hydrolytic reagents and oxidizing reagents. Personal care or household care compositions are prepared by adding the cationic, oxidized polysaccharide to a personal care or household composition containing at least one active ingredient other than the cationic, oxidized polysaccharide of this invention.

61 Claims, No Drawings

CATIONIC, OXIDIZED POLYSACCHARIDES IN CONDITIONING APPLICATIONS

FIELD OF THE INVENTION

The present invention relates to use of cationic oxidized polysaccharide compositions in personal care and household compositions.

BACKGROUND OF THE INVENTION

Cationic polysaccharides and other polymers have been used widely in personal care and household products to perform a function in the final product, ranging from thickening to conditioning of a substrate. Depending on the application, the substrate can be skin, hair, or textile material.

Cationic polysaccharides are used in haircare products to provide conditioning to the hair. In skincare products, these same polymers can provide conditioning effects to the skin. When incorporated into detergent and fabric softening formulations, these same polymers can provide conditioning, softening, anti-pilling, color retention and antistatic characteristics to fabrics.

Hair conditioning agents perform their functions at the cuticle, or outer sheath of keratinized scales on the surface of the hair fiber. The cuticle's scales are arranged in overlapping fashion like the shingles on a roof. The cell structure of the cuticle is composed of an A layer, the exocuticle, and a B layer, the endocuticle. The clear outer A layer, composed of sulfur-containing proteins, protects the hair from chemical, physical, and environmental damage. Consequently, the condition of the cuticle determines the condition of the hair, and hair-conditioning products are directed toward enhancing and restoring the cuticle shaft layer. An intact cuticle is responsible for the strength, shine, softness, smoothness, and manageability of hair. (Conditioning Agents for Hair & Skin, Ed. R. Schueller and P. Romanowski, Marcel Dekker, Inc., NY, N.Y., 1999.)

Wet and dry combability measurements are typical test methods used to measure conditioning-performance in shampoo and conditioner applications. Commercial cationic conditioning polymers in the marketplace have been reported to reduce the wet combing force experienced on combing wet hair by 30%-50% relative to the shampoo containing no polymer.

Historically, only high molecular weight cationic polymers have been used in cleansing products, and it has been suggested that only high molecular weight cationic polymers can deliver the conditioning effect desired in cleansing systems (V. Andre, R. Norenberg, J. Rieger, P. Hoessel, Proceedings, XXIst IFSCC International Congress 2000, Berlin, p. 189-199). However, the high molecular weight cationic guar conditioning polymers, available in the marketplace, have their drawbacks, such as incompatibility with surfactant systems used in shampoo, bodywash, conditioners, skin care, sun care, laundry products etc. In addition, they contribute to the final product viscosity, which may not be desirable. High molecular weight cationic guar polymers are also known to be difficult to disperse and dissolve in aqueous solution.

U.S. Pat. No. 6,210,689 B1 discloses the use of an amphoteric guar gum composition that contains cationic and anionic groups attached to its backbone for treating keratin substances. This composition is used in aqueous systems of cosmetics such as shampoos, topical sprays, dental care products and products containing fragrances and/or antimicrobial agents.

U.S. Pat. No. 5,756,720 describes a process for producing a polygalactomannan composition having nonionic and cationic groups attached to the backbone. This patent describes the achievement of high optical clarity in cleansing surfactant formulations with this composition. The hydroxypropyl cationic polygalactomannans of this composition, however, have been found lacking in conditioning performance, as described in WO 99/36054.

U.S. Pat. No. 5,489,674 describes a process for preparing polygalactomannan gum and a polygalactomannan gum composition prepared by a specific process that includes aqueous alcohol processing. The product is described as giving 85-100% transmittance at wavelengths between 500-600 nm at 0.5 part polymer in 100 parts of an aqueous solution. The use of this material in personal care applications is disclosed.

JP Application Hei 10 [1998]-36403 discloses a cosmetic composition that uses a polygalactomannan degradation product that has 80% or higher of its molecular weight distribution within the range of 4,500 to 35,000 for use in hair and skin care products.

U.S. Pat. Nos. 5,480,984 and 6,054,511 disclose an aqueous, high solids low viscosity polysaccharide composition and a method of making the composition by reacting a polysaccharide and hydrogen peroxide oxidizing agent to produce a product with a solid content of about 20% to about 50% and a viscosity below 9500 mPa·s at 25° C. Cellulose ethers, guar, and guar derivatives are disclosed as polysaccharides that have a wide variety of uses such as in cosmetics.

U.S. Patent application serial number 20030199403 A1 discloses a shampoo composition of a detersive surfactant, a cationic guar derivative, and an aqueous carrier. The cationic guar derivative has a charge density of from about 1.25 meq/g to about 7 meq/g and a molecular weight of from about 10,000 to about 10,000,000.

Cationic HEC, such as Ucare Polymer JR400™ having a high cationic substitution has been cited by the manufacturer as causing "buildup" problems after repeated use. One manufacturer has recommended the use of cationic HEC having lower cationic substitution levels to eliminate buildup issues ("Cationic Conditioners that Revitalize Hair and Skin", Amerchol Product Literature, WSP801, July, 1998). Buildup has been defined by this manufacturer as the binding of a polymer to a substrate, making it more difficult to remove the polymer from the substrate in subsequent cleansing treatments.

A need still exists in the marketplace for a cationic conditioning polymer that has broad surfactant compatibility, and can deliver personal care and household formulations with good conditioning performance. The present invention meets this need by providing cationic conditioning polymers that not only have good conditioning performance with broad surfactant compatibility, but also are economical to formulate in compositions where clarity is not necessarily an issue.

BRIEF SUMMARY OF THE INVENTION

The present invention relates to personal care and household compositions comprising at least one cationic, oxidized polysaccharide or derivative thereof having a weight average molecular weight (Mw) with a lower limit of 50,000 and an upper limit of 1,000,000 having aldehyde functionality at a level of at least 0.001 meq/gram.

The cationic, oxidized polysaccharide or derivative thereof can preferably have a Brookfield viscosity at 10 wt. % solids of the polysaccaride at 25° C. using a spindle 4 at 30 rpm with a lower limit of 30 cps and an upper limit of 20,000 cps, with the proviso that if the viscosity of the polysaccharide is above 20,000 cps, then the Brookfield viscosity is measured at a solids content of 10 wt. % at 25° C. using a spindle 4 at 0.3 rpm has a lower limit of 20,000 cps and an upper limit of 2,000,000. This viscosity range is particularly preferred with cationic, oxidized polygalactomannans.

This invention further relates to a method for making a personal care or household composition comprising adding a cationic, oxidized polysaccharide to a personal care or household composition containing at least one active ingredient other than the cationic, oxidized polysaccharide of this invention.

DETAILED DESCRIPTION OF THE INVENTION

In accordance to this invention, it has surprisingly been found that the cationic oxidized polysaccharides of this invention can deliver the conditioning or lubricating effect desired in cleansing products such as shampoos, two-in-one shampoos (i.e., cleans and conditions the hair), three-in-one shampoos (i.e., cleans, conditions, and delivers styling), conditioners, shower gels, liquid soaps, bodywash, styling products, shave gels/creams, body cleansers, and bar soaps. The polymers of this invention deliver the conditioning or lubricating properties of good wet and dry combing force reduction to hair when incorporated into a broad range of cleansing shampoo surfactant systems where such properties are desired. The polymers of this invention also deliver the conditioning or lubricating property of softer feel to skin when incorporated in skin care, sun care, bodywashes, body cleansers, and bar soaps.

Similar conditioning or lubricating effects are expected in surfactant-based household cleansing product formulations where conditioning performance is desired, such as dish detergents, laundry detergent, fabric softeners, and antistatic products. Conditioning in fabric softeners and in laundry detergent refers to imparting a softer feel, anti-pilling, color retention to fabric and eliminating static effects.

The cationic functionality of the polysaccharide or derivatized polysaccharide can be added to the backbone by known methods. For example, the polysaccharide material can be reacted for a sufficient time and at a sufficient temperature with tertiary amino or quaternary ammonium alkylating reagents, such 2-dialkylaminoethyl chloride and quaternary ammonium compounds such as 3-chloro-2-hydroxypropyltrimethylammonium chloride, and 2,3-epoxy-propyltrimethylammonium chloride. Preferred examples include glycidyltrialkylammonium salts and 3-halo-2-hydroxypropyltrialkylammonium salts such as glycidyltrimethylammonium chloride, glycidyltriethylammonium chloride, gylcidyltripropylammonium chloride, glycidylethyldimethylammonium chloride, glycidyldiethylmethylammonium chloride, and their corresponding bromides and iodides; 3-chloro-2-hydroxypropyltrimethylammonium chloride, 3-chloro-2-hydroxypropyltriethylammonium chloride, 3-chloro-2-hydroxypropyltripropylammonium chloride, 3-chloro-2-hydroxypropylethyldimethylammonium chloride, and their corresponding bromides and iodides; and quaternary ammonium compounds such as halides of imidazoline ring containing compounds.

The cationic polysaccharides may also contain other substituent groups such as nonionic substituents, i.e., hydroxyalkyl wherein the alkyl represents a straight or branched hydrocarbon moiety having 1 to 30 carbon atoms (e.g., hydroxyethyl, hydroxypropyl, hydroxybutyl) or anionic substituents, such as carboxymethyl groups are optional. These optional substituents are linked to the polysaccharide polymer by the reaction with reagents such as (1) alkylene oxides (e.g., ethylene oxide, propylene oxide, butylene oxide) to obtain hydroxyethyl groups, hydroxypropyl groups, or hydroxybutyl groups, or with (2) chloromethyl acetic acid to obtain a carboxymethyl group. The process for preparing derivatized polygalactomannan is well known in the art.

Polysaccharides can be oxidized by several known reagent and methods, such as (1) by biochemical oxidants, such as galactose oxidase, (2) chemical oxidants, such as hydrogen peroxide, (3) a physical methods using high speed agitation and shearing machines, (4) thermal methods, and (5) mixtures of these reagents and methods.

In accordance with this invention, the cationic, oxidized polysaccharides used to make personal care or household compositions with good conditioning properties are preferably made by using oxidative reagent either alone or in combination with other reagents, including biochemical reagents, that reduce molecular weight and/or introduce oxidized functional groups. In order to achieve optimum results, it is necessary to include the oxidative step in the process either completely or alternately with other reagents.

Oxidative agents include any reagent that incorporates oxygen atoms into the polymer structure. Some oxidizing reagents can also act to reduce the molecular weight of the polymer. Examples of these dual function oxidizing agents are peroxides, peracids, persulfates, permanganates, perchlorates, hypochlorite, and oxygen. Examples of biochemical oxidative agents that do not reduce molecular weight are oxidases. Specific examples of oxidases useful in this invention are galactose oxidase, and other biochemical oxidizing agents known to those skilled in the art.

The incorporation of an oxidizing agent into the process for preparing the products of this invention has been found to be useful, in that cationic polymers prepared with the use of an oxidizing agent have greater solubility in a broader range of surfactant systems commonly used in personal care and household compositions than cationic polymers that have not been treated with an oxidizing agent.

As mentioned above, incorporation of an oxidizing agent into the process for preparing the products that are used to make the personal care and household compositions of this invention introduces aldehyde groups into the polymer composition. These polymers have been found to contain at least 0.001 milliequivalents aldehyde per gram (meq/g) of polysaccharide. The upper limit of the aldehyde content is about 1.0 meq/g.

In accordance with the present invention, the cationic, oxidized polysaccharide or derivative thereof generally has a cationic degree of substitution (DS) lower limit of about 0.001 and an upper limit of about 3.0. Preferably, the lower limit of the cationic DS is 0.01, and more preferably 0.05. Preferably, the upper limit of the cationic DS is 2.0, more preferably 1.0, and even more preferably 0.25. The cationic, oxidized polysaccharide or derivative thereof of the present invention generally has a weight average molecular weight (Mw) with a lower limit of about 50,000 and an upper limit of about 1,000,000. Preferably, the lower limit of the Mw is about 75,000 and more preferably about 100,000. The upper limit of the Mw preferably is about 600,000, more preferably about 300,000, and even more preferably about 150,000.

In accordance with the present invention, the personal care active ingredient must provide some benefit to the user's body. Personal care products includes hair care, skincare, sun care, and oral care products. Examples of substances that may suitably be included, but not limited to, in the personal care products according to the present invention are as follows:

1) Perfumes, which give rise to an olfactory response in the form of a fragrance and deodorant perfumes which in addition to providing a fragrance response can also reduce body malodor;

2) Skin coolants, such as menthol, menthyl acetate, menthyl pyrrolidone carboxylate N-ethyl-p-menthane-3-carboxamide and other derivatives of menthol, which give rise to a tactile response in the form of a cooling sensation on the skin;

3) Emollients, such as isopropylmyristate, silicone materials, mineral oils and vegetable oils which give rise to a tactile response in the form of an increase in skin lubricity;

4) Deodorants other than perfumes, whose function is to reduce the level of or eliminate micro flora at the skin surface, especially those responsible for the development of body malodor. Precursors of deodorants other than perfume can also be used;

5) Antiperspirant actives, whose function is to reduce or eliminate the appearance of perspiration at the skin surface;

6) Moisturizing agents, that keeps the skin moist by either adding moisture or preventing from evaporating from the skin;

7) Cleansing agents, that removes dirt and oil from the skin;

8) Sunscreen active ingredients, that protect the skin and hair from UV and other harmful light rays from the sun. In accordance with this invention a therapeutically effective amount will normally be from 0.01 to 10% by weight, preferable 0.1 to 5% by weight of the composition;

9) Hair treatment agents, that conditions the hair, cleans the hair, detangles hair, acts as styling agent, volumizing and gloss agents, anti-dandruff agent, hair growth promoters, hair dyes and pigments, hair perfumes, hair relaxer, hair bleaching agent, hair moisturizer, hair oil treatment agent, and antifrizzing agent;

10) Oral care agents, such as dentifrices and mouth washes, that clean, whiten, deodorize and protect the teeth and gum;

11) Denture adhesives that provide adhesion properties to dentures;

12) Shaving products, such as creams, gels and lotions and razor blade lubricating strips;

13) Tissue paper products, such as moisturizing or cleansing tissues;

14) Beauty aids, such as foundation powders, lipsticks, and eye care; and

15) Textile products, such as moisturizing and/or cleansing wipes, and diapers;

16) Nail care products such as nail polish.

In accordance with the present invention, the household care active ingredient must provide some benefit to the user. Examples of substances that may suitably be included, but not limited to, according to the present invention are as follows:

1) Perfumes, which give rise to an olfactory response in the form of a fragrance and deodorant perfumes which in addition to providing a fragrance response can also reduce odor;

2) Insect repellent agent whose function is to keep insects from a particular area or attacking skin;

3) Bubble generating agent, such as surfactants which generates foam or lather;

4) Pet deodorizer such as pyrethrins which reduces pet odor;

5) Pet shampoo agents and actives, whose function is to remove dirt, foreign material and germs from the skin and hair surfaces and conditions the skin and hair;

6) Industrial grade bar, shower gel, and liquid soap actives that remove germs, dirt, grease and oil from skin, sanitizes skin, and conditions the skin;

7) All purpose cleaning agents, that remove dirt, oil, grease, germs from the surface in areas such as kitchens, bathroom, public facilities;

8) Disinfecting ingredients that kill or prevent growth of germs in a house or public facility;

9) Rug and Upholstery cleaning actives which lift and remove dirt and foreign particles from the surfaces and also deliver softening and perfumes;

10) Laundry softener actives which reduces static and makes fabric feel softer;

11) Laundry detergent ingredients which remove dirt, oil, grease, stains and kills germs;

12) Dishwashing detergents which remove stains, food, germs;

13) Toilet bowl cleaning agents which removes stains, kills germs, and deodorizes;

14) Laundry prespotter actives which helps in removing stains from clothes;

15) Fabric sizing agent which enhances appearance of the fabric;

17) Vehicle cleaning actives which removes dirt, grease, etc. from vehicles and equipment;

18) Lubricating agent which reduces friction between parts; and

19) Textile products, such as dusting or disinfecting wipes.

The above list of personal care and household active ingredients are only examples and are not a complete lists of active ingredients that can be used. Other ingredients that are used in these types of products are well known in the industry. In addition to the above ingredients conventionally used, the composition according to the present invention can optionally also include, but not limited to, ingredients such as a colorant, preservative, antioxidant, nutritional supplements, alpha or beta hydroxy acid, activity enhancer, emulsifiers, functional polymers, viscosifying agents (such as salts, i.e., NaCl, $NH_4Cl$ & KCl, water-soluble polymers, i.e., hydroxyethylcellulose, and fatty alcohols, i.e., cetyl alcohol; water-swellable materials, such as clay and silica), alcohols having 1-6 carbons, fats or fatty compounds (i.e., fatty amides and fatty acid esters and fatty alcohol polyethylene glycol ethers), antimicrobial compound, zinc pyrithione, silicone material, hydrocarbon polymer, emollients, oils, surfactants, medicaments, flavors, fragrances, suspending agents (i.e., xanthan gum, carbomer, clay, and silica), and mixtures thereof.

In accordance with the present invention, examples of functional polymers that can be used in blends with the cationic, oxidized polysaccharides or derivatives thereof of this invention include water-soluble polymers such as acrylic acid homopolymers such as Carbopol® product and anionic and amphoteric acrylic acid copolymers, vinylpyrrolidone homopolymers and cationic vinylpyrrolidone copolymers; nonionic, cationic, anionic, and amphoteric cellulosic polymers such as hydroxyethylcellulose, hydroxypropylcellulose, carboxymethylcellulose, hydroxypropylmethylcellulose, cationic hydroxyethylcellulose, cationic carboxymethylhydroxyethylcellulose, and cationic hydroxypropylcellulose; clay; acrylamide homopolymers and cationic, amphoteric, and hydrophobic acrylamide copolymers, polyethylene glycol polymers and copolymers, hydrophobic polyethers, hydrophobic polyetheracetals, hydrophobically-modified polyetherurethanes and other polymers referred to as associative polymers, hydrophobic cellulosic polymers, polyethyleneoxide-propylene oxide copolymers, and nonionic, anionic, hydrophobic, amphoteric, and cationic polysaccharides such as xanthan, chitosan, carboxymethyl guar, alginates, hydroxypropyl guar, carboxymethyl guar hydroxypropyltrimethylammonium chloride, guar hydroxypropyltrimethylammonium chloride, hydroxypropyl guar hydroxypropyltrimethylammonium chloride.

In accordance with the invention, the silicone materials which can be used are, in particular, polyorganosiloxanes that are insoluble in the composition and can be in the form of polymers, oligomers, oils, waxes, resins, or gums.

The organopolysiloxanes are defined in greater detail in Walter Noll's "Chemistry and Technology of Silicones" (1968) Academic Press. They can be volatile or non-volatile.

If volatile, the silicones are more particularly chosen from those having a boiling point of between 60° C. and 260° C., and even more particularly from:

(i) cyclic silicones containing from 3 to 7 and preferably from 4 to 5 silicon atoms. These are, for example, octamethylcyclotetrasiloxane sold in particular under the name "Volatile Silicone 7207" by Union Carbide or "Silbione 70045 V 2" by Rhone-Poulenc, decamethylcyclopentasiloxane sold under the name "Volatile Silicone 7158" by Union Carbide, and "Silbione 70045 V 5" by Rhone-Poulenc, and mixtures thereof.

Mention may also be made of mixtures of cyclic silicones with organosilicone compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy) neopentane;

(ii) linear volatile silicones having 2 to 9 silicon atoms and having a viscosity of less than or equal to $5 \times 10^{-6}$ m$^2$/s at 25° C. An example is decamethyltetrasiloxane sold in particular under the name "SH 200" by Toray Silicone company. Silicones belonging to this category are also described in the article published in Cosmetics and Toiletries, Vol. 91, Jan. 76, pp. 27-32, Todd & Byers "Volatile Silicone Fluids for Cosmetics".

Non-volatile silicones, and more particularly polyarylsiloxanes, polyalkylsiloxanes, polyalkylarylsiloxanes, silicone gums and resins, polyorganosiloxanes modified with organofunctional groups, and mixtures thereof, are preferably used.

In accordance with the invention, the silicone polymers and resins which can be used are, in particular, polydiorganosiloxanes having high number-average molecular weights of between 200,000 and 1,000,000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Examples of these silicone polymers and resins are as follows:

Polydimethylsiloxane,
polydimethylsiloxanes/methylvinylsiloxane gums,
polydimethylsiloxane/diphenylmethylsiloxane,
polydimethylsiloxane/phenylmethylsiloxane, and
polydimethylsiloxane/diphenylsiloxanemethylvinylsiloxane.

Products which can be used more particularly in accordance with the invention are mixtures such as:

(a) mixtures formed from a polydimethylsiloxane hydroxylated at the end of the chain (referred to as dimethiconol according to the nomenclature in the CTFA dictionary) and from a cyclic polydimethylsiloxane (referred to as cyclomethicone according to the nomenclature in the CTFA dictionary), such as the product Q2 1401 sold by the Dow Corning Company;

(b) mixtures formed from a polydimethylsiloxane gum with a cyclic silicone, such as the product SF 1214 Silicone Fluid from the company General Electric Company; this product is an SF 30 gum corresponding to a dimethicone, having a number-average molecular weight of 500,000, dissolved in SF 1202 Silicone Fluid oil corresponding to decamethylcyclopentasiloxane; and (c) mixtures formed of two PDMSs of different viscosities, and more particularly of a PDMS gum and a PDMS oil, such as the product SF 1236 from the General Electric Company. This product preferably contains 15% SE 30 gum and 85% SF 96 oil.

For a more detailed understanding of the invention, reference can be made to the following examples which are intended as further illustration of the invention and are not to be construed in a limiting sense. All parts and percentages are by weight unless stated otherwise.

EXAMPLES

I. Use of Chemical Oxidative Reagent

Four Step Standard Decomposition Method

Materials:
Cationic polygalactomannan (guar hydroxypropyltrimoniumchloride)—Hercules, Incorporated
CAS#65497-29-2
Fumaric acid, P.A.—Acros/Fisher Scientific,
CAS#110-17-8
Dow Corning 200® Fluid, 50 CST.—silicone oil—for Neslab oil—bath
CAS#63448-62-9
Kathon® CG stabilizing biocide/preservative—Rohm and Haas Co,
CAS# mixture, see MSDS
Hydrogen Peroxide, 30%—JTBaker—CAS#7722-84-1
EM Quant Peroxide Test Strip from EM Science.

Depolymerization of Cationic Polygalactomannan:

|  | First Step Charge | Second Step charge | Third Step charge | Fourth Step charge | Total Final charge |
|---|---|---|---|---|---|
| Deionized Water | 2400.0 | q.s. to 2500 | q.s. to 2500 | q.s. to 2500 | 2097.5 |
| Hydrogen peroxide, 1.0% | 37.5 | 37.5 | 37.5 | 37.5 | 150.0 |
| Cationic Polygalactomannan w/2.0% fumaric acid added | 62.5 | 62.5 | 62.5 | 62.5 | 250.0 |
|  | 2500.0 | 2500.0 | 2500.0 | 2500.0 | 2497.5 |
| Kathon CG |  |  |  |  | 2.5 |
| Total | 2500.0 | 2500.0 | 2500.0 | 2500.0 | 2500.0 |

Note:
In this formulation, hydrogen peroxide is used at 60 (parts by weight) pbw 1.0% $H_2O_2$ per 100 pbw Polygalactomannan.

Procedure:

The deionized water of the first step was weighed and charged into the beaker and the beaker was suspended in the bath using a chain clamp. A Caframo Stirrer Model BDC-3030 was assembled with a Caframo "U"-shaped 4" (Anchor) Paddle and a digital alarm thermometer probe in the batch. The beaker was covered with saran film to minimize water loss. The water was heated to 85-90° C. in the oil bath set at ~95° C. while stirring at ~50 rpm. The bath temperature was adjusted as necessary to maintain the batch temperature at 85-90° C. An additional Caframo mixer Model RZR-1 was used with a 2" propeller blade at low speed in the bath to improve the oil circulation.

The stirrer speed was increased to ~100 rpm, as volume permitted, and ¼ of the total peroxide charge was added to the beaker using an appropriate size weighed hypodermic syringe, by injecting the peroxide through the saran covering. The contents of the beaker was allowed to mix ~5 minutes. Then the covering on the beaker was removed and very slowly ¼ of the total cationic polygalactomannan charge was sifted into the beaker while mixing. The stirring speed of the stirrer was adjusted to maintain adequate vortex speed. Some lumping may occur, especially during the first polygalactomannan addition; however, small lumps will dissolve as viscosity increases. The covering was replaced and mixing was continued at a temperature of 85-90° C. until viscosity had decreased enough to permit the next polymer addition.

The addition of peroxide and polymer were repeated for a total of four times, allowing time for the polymer to dissolve and the viscosity to decrease before the next incremental addition, until the total $H_2O_2$ and polygalactomannan charges were added. If necessary, the water level in the beaker was adjusted at each interval for water loss. After the last addition, mixing was continued for one hour; then the amount of residual peroxide was checked using the EM Quant Peroxide Test Strips. The mixer was stopped and a small hole was made in the saran where the sensing area of the test strip was immersed into the solution for one second. Excess material was shaken off the test strip and, after 15 seconds, the color of the sensing area of the test strip was compared to the scale on the container. The reaction was continued until $H_2O_2$ level was <50 ppm. Note: The sensing area of the test strips will probably turn dark brown due to the high level of peroxide present. In that case, carefully extract a small sample (~5 g) of the solution and dilute with an amount of room temperature deionized water, enough to permit readings on the test strip within its range of detection.

The bath heat was turned off and the oil was diverted through the Neslab FTC-350 cooler. When the oil was cooled enough, the beaker was carefully removed from the bath (slippery from silicone oil) and the net weight of the batch was measured. The required amount of make-up water was determined, the make-up water was pre-mixed with 1.0% Germaben II product, and the water/Germaben II mixture was added while stirring manually. When the solution was extremely viscous, the beaker was returned to the bath for the addition of stabilizing biocide and make-up water with mechanical stirring. The content of the beaker was pack-out while warm into appropriate containers for retaining, stability testing of pH, Brookfield viscosity, and analyses as necessary.

Combing Test

The wet comb and dry comb measurements were performed on an Instron instrument using mildly bleached European hair tresses that had been shampooed with a mild anionic surfactant-based shampoo or a nonionic surfactant shampoo.

The percent reduction in wet comb and dry comb energy is defined as shown in equation (1). The energy needed to comb a tress after shampooing with a shampoo containing cationic polymer was subtracted from the energy needed to comb a tress that had been shampooed twice with 4.5 wt % sodium lauryl sulfate (SLS) solution. This remainder was then divided by the energy needed to comb the tress washed with the SLS solution. The value was multiplied by 100 and was called the percent reduction in combing force. The percent reduction was typically a positive number if the cationic conditioning polymer conditions the hair.

$$[Energy(No\ Polymer)(gf\text{-}mm) - Energy(with\ Polymer)] / Energy(No\ Polymer)] \times 100 = Percent\ Reduction\ in\ Combing\ Energy \quad (1)$$

Example 1

The above-mentioned Standard Decomposition Method was used. About 935 grams of water was placed in a 1500 ml beaker and placed in an oil bath set at a temperature of about 120° C. The beaker was then heated to a temperature of about 85-95° C. in the oil bath and maintained at this temperature. A double 2" propeller blade mixer was inserted into the beaker and a small portion of N-Hance® 3205 cationic guar product (Hercules Incorporated, Wilmington, Del.) was added while stirring. Then a small amount of peroxide was added to the beaker while continuing to mix. The viscosity of this mixture became thick and it was continued to be mixed at 85-95° C. until the viscosity became low enough for the next portions of the polymer and peroxide additions. Three additional portions of the polymer and peroxide were repeated until the full amount of the polymer and peroxide were completed. During this incremental addition of the polymer and peroxide some of the water evaporated. Hence, at the end of the additions, the water level was adjusted for water loss. The amount of residual peroxide was periodically checked in the beaker using test strips and the reaction was continued until less than 50 ppm of peroxide remained. The oil bath was then shut down and the beaker was cooled to ambient temperatures. The Germaben® II stabilizing biocide/preservative (ISP Incorporated, Wayne, N.J.) was added to the beaker.

The below noted Table 1 (experiment A to F) sets forth the ingredients for this experiment.

TABLE 1

Degradation of Cationic Guar Polymers

|  | A | B | C | D | E | F |
|---|---|---|---|---|---|---|
| Deionized water | 935.07 | 947.36 | 960.00 | 965.15 | 967.74 | 970.35 |
| N-Hance 3205 | 25.97 | 26.32 | 26.67 | 26.81 | 26.88 | 26.95 |
| Hydrogen Peroxide - 6.0% | 38.96 | 26.32 | 13.33 | 8.04 | 5.38 | 2.70 |
|  | 1000.00 | 1000.00 | 1000.00 | 1000.00 | 1000.00 | 1000.00 |
| N-Hance 3205 | 25.97 | 26.32 | 26.67 | 26.81 | 26.88 | 26.95 |
| Hydrogen Peroxide - 6.0% | 38.96 | 26.32 | 13.33 | 8.04 | 5.38 | 2.70 |
| N-Hance 3205 | 25.97 | 26.32 | 26.67 | 26.81 | 26.88 | 26.95 |
| Hydrogen Peroxide - 6.0% | 38.96 | 26.32 | 13.33 | 8.04 | 5.38 | 2.70 |

TABLE 1-continued

Degradation of Cationic Guar Polymers

|  | A | B | C | D | E | F |
|---|---|---|---|---|---|---|
| N-Hance 3205 | 25.97 | 26.32 | 26.67 | 26.81 | 26.88 | 26.95 |
| Hydrogen Peroxide - 6.0% | 38.96 | 26.32 | 13.33 | 8.04 | 5.38 | 2.70 |
| Germaben II | 10.00 | 10.00 | 10.00 | 10.00 | 10.00 | 10.00 |
|  | 1204.79 | 1167.92 | 1130.00 | 1114.55 | 1106.78 | 1098.95 |

Example 2

The procedure noted above in Example 1 was followed for experiments G, H, and I except that the oil bath temperature was adjusted to maintain sample temperature at about 85-90° C. and a 1.0% hydrogen peroxide solution was used in place of a 6.0% solution. Also, the order of addition of the polymer and peroxide was reversed with the peroxide being added first and then the polymer incrementally. Table 2, noted below, sets forth the ingredients for experiments G, H, and I.

Example 3

In the following experiment (Table 2 experiments J, K and L), the procedure used in Example 2 above was used, except that N-Hance® 3215 product (with fumaric acid) was used in place of N-Hance® 3205 polymer.

TABLE 2

Degradation of Cationic Guar Polymers

| | G | H | I | | J | K | L |
|---|---|---|---|---|---|---|---|
| Deionized water | 957.44 | 963.59 | 969.83 | | 957.44 | 963.59 | 969.83 |
| Hydrogen Peroxide - 1.0% | 15.96 | 9.64 | 3.23 | | 15.96 | 9.64 | 3.23 |
| N-Hance 3205 | 26.60 | 26.77 | 26.94 | N-Hance 3215 w/fumaric acid | 26.60 | 26.77 | 26.94 |
| | 1000.00 | 1000.00 | 1000.00 | | 1000.00 | 1000.000 | 1000.00 |
| Hydrogen Peroxide - 1.0% | 15.96 | 9.64 | 3.23 | | 15.96 | 9.64 | 3.23 |
| N-Hance 3205 | 26.60 | 26.77 | 26.94 | N-Hance 3215 w/fumaric acid | 26.60 | 26.77 | 26.94 |
| Hydrogen Peroxide - 1.0% | 15.96 | 9.64 | 3.23 | | 15.96 | 9.64 | 3.23 |
| N-Hance 3205 | 26.60 | 26.77 | 26.94 | N-Hance 3215 w/fumaric acid | 26.60 | 26.77 | 26.94 |
| Hydrogen Peroxide - 1.0% | 15.96 | 9.64 | 3.23 | | 15.96 | 9.64 | 3.23 |
| N-Hance 3205 | 26.60 | 26.77 | 26.94 | N-Hance 3215 w/fumaric acid | 26.60 | 26.77 | 26.94 |
| Germaben II | 10.00 | 10.00 | 10.00 | | 10.00 | 10.00 | 10.00 |
| | 1111.08 | 1092.46 | 1073.57 | | 1111.08 | 1092.46 | 1073.57 |

Example 4

The same procedure used in Example 3 was followed in this Example 4 for experiments M, N, and O series and noted in Table 3 except that (a) for experiment M, Jaguar® C-13-S cationic guar product (Rhodia Incorporated, Cranberry, N.J.) was used, (b) for experiment N, Jaguar® C-162 cationic hydroxypropyl guar product (Rhodia Incorporated, Cranberry, N.J.) was used and (c) for experiment O, N-Hance® 3215 cationic guar product (Hercules Incorporated, Wilmington, Del.) degraded with heat only and no peroxide was used.

Experiment O was extremely viscous after the first polymer addition. Second and third polymer additions were cut in half, but the viscosity remained extremely high. The preparation was discontinued; the Germaben® II preservative was not added. This example demonstrated that thermal degradation, in the absence of hydrogen peroxide, proceeds very slowly.

TABLE 3

Degradation of Cationic Guar Polymers

| | M | N | O |
|---|---|---|---|
| Deionized water | 963.59 | 963.59 | 972.97 |
| Hydrogen Peroxide - 1.0% | 9.64 | 9.64 | — |
| Jaguar C-13-S | 26.77 | — | — |
| Jaguar C-162 | — | 26.77 | — |
| N-Hance 3215 | | | 27.03 |
| Hydrogen Peroxide - 1.0% | 9.64 | 9.64 | — |
| Jaguar C-13-S | 26.77 | — | — |

TABLE 3-continued

Degradation of Cationic Guar Polymers

| | M | N | O |
|---|---|---|---|
| Jaguar C-162 | — | 26.77 | — |
| N-Hance 3215 | | | * 13.52 |
| Hydrogen Peroxide - 1.0% | 9.64 | 9.64 | — |
| Jaguar C-13-S | 26.77 | — | — |
| Jaguar C-162 | — | 26.77 | — |
| N-Hance 3215 | | | * 13.52 |
| Hydrogen Peroxide - 1.0% | 9.64 | 9.64 | — |
| Jaguar C-13-S | 26.77 | — | — |
| Jaguar C-162 | — | 26.77 | — |
| Germaben II | 10.00 | 10.00 | — |
| | 1092.46 | 1092.46 | 972.97 |

Example 5

The same preparation and procedure used for Example 2 were used in this Example 5 for experiments P, Q and R and were reported in Table 4.

TABLE 4

Degradation of Cationic Guar Polymers

|  | P | Q | R |
|---|---|---|---|
| Deionized water | 957.44 | 963.59 | 969.83 |
| Hydrogen Peroxide - 1.0% | 15.96 | 9.64 | 3.23 |
| N-Hance 3205 | 26.60 | 26.77 | 26.94 |
|  | 1000.00 | 1000.00 | 1000.00 |
| Hydrogen Peroxide - 1.0% | 15.96 | 9.64 | 3.23 |
| N-Hance 3205 | 26.60 | 26.77 | 26.94 |
| Hydrogen Peroxide - 1.0% | 15.96 | 9.64 | 3.23 |
| N-Hance 3205 | 26.60 | 26.77 | 26.94 |
| Hydrogen Peroxide - 1.0% | 15.96 | 9.64 | 3.23 |
| N-Hance 3205 | 26.60 | 26.77 | 26.94 |
| Germaben II | 10.00 | 10.00 | 10.00 |
|  | 1111.08 | 1092.46 | 1073.57 |

Example 6

The same procedure used for experiments J, K, and L series in Example 3 was used for the experiments S, T, U, V, W, and X of this Example 6 and were reported in Table 5. For Experiments X and Y, the tap water concentration is in gallons and all material concentrations are in pounds. For experiments W and X, N-Hance 3215 water-wet cationic guar splits were used in place of N-Hance 3215 cationic guar powder and hydrochloric acid was used in place of fumaric acid to neutralize the cationic guar splits to a pH of 6.5. Sodium metabisulfite was added at the end of the reaction to decompose residual peroxide. The product of Experiment X was further treated with sodium hydroxide at pH 8 for 30 minutes, followed by neutralization with dilute hydrochloric acid. The product from experiment V had an aldehyde content of 0.035 meq/gram and Mw of 61,000. The product from experiment U had a molecular weight of 50,400. For Experiment Y, all of the hydrogen peroxide and the malic acid were added after reactor heat up to 90° C. The N-Hance cationic guar was added as a 20% solids slurry to the reactor. The reaction pH was maintained at 6, and sodium metabisulfite was added at the end of the reaction to decompose residual hydrogen peroxide. The product of Experiment Y was further treated with a nitrogen sparge after pH adjustment to pH of 7, followed by addition of the preservative and additional acids to bring the pH to approximately 6.

For Experiment Z, the same procedure in experiment V was followed, using a high molecular weight cationic guar PRECURSOR 2 (cationic DS of 0.5), blended with fumaric acid. Experiments AA and AB used high molecular weight cationic guar PRECURSOR 3 (999,145 Dalton, cationic DS of 0.9), reacted at 90° C. in a one stage reaction, adding the hydrogen peroxide to the water at temperature, followed by addition of the cationic guar. Sodium metabisulfite was added to destroy excess hydrogen peroxide.

TABLE 5

Peroxide Degradation of Cationic Guar Polymers

|  | S | T | U | V | W | X | Y | Z | AA | AB | AC |
|---|---|---|---|---|---|---|---|---|---|---|---|
| Tap Water |  |  |  |  |  | 278 | 20.2 |  |  |  |  |
| Deionized water | 957.44 | 963.59 | 2412.3 | 2412.3 | 2300 |  |  | 1468 | 875 | 873 | 919 |
| Hydrogen Peroxide - 1.0% | 15.96 | 9.64 |  |  |  |  |  | 22.5 | 6.6 | 60 | 21 |
| Hydrogen Peroxide - 6.0% |  |  | 18.75 | 18.75 | 18.7 | 2.8 |  |  |  |  |  |
| Hydrogen Peroxide - 35% |  |  |  |  |  |  | 2.26 lbs |  |  |  |  |
| 2 N HCl(aq) |  |  |  |  |  | 1.27 |  |  |  |  |  |
| Malic Acid |  |  |  |  |  |  | 0.67- lbs |  |  |  |  |
| N-Hance 3000 |  |  |  |  |  |  |  |  |  |  | 50 |
| N-Hance 3215 w/fumaric acid | 26.60 | 26.77 | 68.9 | 68.9 |  |  |  |  |  |  |  |
| N-Hance 3215 (20% slurry) |  |  |  |  |  |  | 190 lbs |  |  |  |  |
| N-Hance 3215 splits (39.5% solids) |  |  |  |  | 62.4 | 23.45 |  |  |  |  |  |
| PRECURSOR 2 w/ fumaric acid |  |  |  |  |  |  |  | 18.75 |  |  |  |
| PRECURSOR 3 |  |  |  |  |  |  |  |  | 56.5 | 56.5 |  |
| Hydrogen Peroxide - 1.0% | 15.96 | 9.64 |  |  |  |  |  | 22.5 |  |  | 10.55 |
| Hydrogen Peroxide - 6.0% |  |  | 18.75 | 18.75 | 18.7 | 2.8 |  |  |  |  |  |
| 2 N HCl(aq) |  |  |  |  |  | 3.33 |  |  |  |  |  |
| N-Hance 3215 w/fumaric acid | 26.60 | 26.77 | 68.9 | 68.9 |  |  |  |  |  |  |  |
| N-Hance 3215 splits |  |  |  |  | 62.4 | 23.45 |  |  |  |  |  |
| PRECURSOR 2 |  |  |  |  |  |  |  | 18.75 |  |  |  |
| Hydrogen Peroxide - 1.0% | 15.96 | 9.64 |  |  |  |  |  | 22.5 |  |  | 11.5 |
| Hydrogen Peroxide - 6.0% |  |  | 18.75 | 18.75 | 18.7 | 2.8 |  |  |  |  |  |
| 2 N HCl(aq) |  |  |  |  |  | 3.33 |  |  |  |  |  |
| N-Hance 3215 w/fumaric acid | 26.60 | 26.77 | 68.9 | 68.9 |  |  |  |  |  |  |  |
| N-Hance 3215 splits |  |  |  |  | 62.4 | 23.45 |  |  |  |  |  |
| PRECURSOR 2 |  |  |  |  |  |  |  | 18.75 |  |  |  |
| Hydrogen Peroxide - 1.0% | 15.96 | 9.64 |  |  |  |  |  | 22.5 |  |  |  |
| Hydrogen Peroxide - 6.0% |  |  | 18.75 | 18.75 | 18.7 | 2.8 |  |  |  |  |  |
| 2 N HCl(aq) |  |  |  |  |  | 3.33 |  |  |  |  |  |
| N-Hance 3215 w/fumaric acid | 26.60 | 26.77 | 68.9 | 68.9 |  |  |  |  |  |  |  |
| N-Hance 3215 splits |  |  |  |  | 62.4 | 23.45 |  |  |  |  |  |
| PRECURSOR 2 |  |  |  |  |  |  |  | 18.75 |  |  |  |

TABLE 5-continued

Peroxide Degradation of Cationic Guar Polymers

|  | S | T | U | V | W | X | Y | Z | AA | AB | AC |
|---|---|---|---|---|---|---|---|---|---|---|---|
| Nipasept Sodium |  |  |  |  |  |  | 0.67 lb |  |  |  |  |
| Phenoxetol |  |  |  |  |  |  | 1.86 lbs |  |  |  |  |
| Kathon CG |  |  | 2 | 2 | 2 | 0.38 |  |  |  |  |  |
| Germaben II | 10.00 | 10.00 | — | — |  |  |  | 15.0 | 10 | 10 | 10 |
| Adipic Acid |  |  |  |  |  |  | 0.22 lbs |  |  |  |  |
| Sodium Metabisulfite |  |  |  |  |  |  | 0.29 lbs |  | 0.19 | 0.19 | 0.375 |
|  | 1111.08 | 1092.46 | 2500 | 2500 | 2625 |  |  | 1633 |  |  |  |

N-Hance 3000 product with cationic DS of 0.06 was depolymerized using the following steps. 918.5 grams of water was heated to about 95° C. Next 31.5 grams of 1.0% hydrogen peroxide was added followed by 50 grams of N-Hance® 3000 product. Stirred for 30 minutes. Next, 15.75 g of 1.0% peroxide was added. Stirred for 90 minutes and then 0.21 g of sodium metabisulfite was added and cooled while mixing. The solution was preserved with 0.5% Phenoxetol® and 0.18% Nipasept® sodium preservatives. Both preservatives are available from Clariant Corporation. The sample had 15 ppm (0.009 meq/g) of aldehyde as determined with E-M Science aldehyde test kit 10036-1 and had molecular weight of 298,000 Dalton.

Example 7

The procedure of Experiment W in Example 6 was repeated using cationic hydroxyethylcellulose (Celquat® SC-240 and Ucare® polymer JR-400) as the cationic polysaccharide instead of cationic guar. These Examples are shown in Table 6. The pH value was maintained at 5-5.5 using 10% sodium hydroxide. Sodium metabisulfite was added to destroy excess hydrogen peroxide at the end of the reaction. BHT and Kathon® CG preservatives were added to preserve the product. The Mw values for the products from Experiments AD, AE, and AF in Table 6 were, 90,000, 179,000, and 46,500. The procedure for experiment AF used the product from experiment AD and only one addition of hydrogen peroxide.

TABLE 6

Degradation of Cationic Hydroxyethyl Cellulose Polymers

|  | AD | AE | AF |
|---|---|---|---|
| Deionized water | 1173 | 1172 |  |
| Hydrogen Peroxide - 30.0% | 4.33 | 2.16 |  |
| Celquat SC-240 | 38.6 | — |  |
| Polymer JR-400 | — | 31 |  |
| Product of Experiment A |  |  | 100 |
| Hydrogen Peroxide - 30.0% | 4.33 | 2.16 | 0.5 |
| Celquat SC-240 | 38.6 | — |  |
| Polymer JR-400 | — | 31 |  |
| Hydrogen Peroxide - 30.0% | 4.33 | 2.16 |  |
| Celquat SC-240 | 38.6 | — |  |
| Polymer JR-400 | — | 31 |  |
| Hydrogen Peroxide - 30.0% | 4.33 | 2.16 |  |
| Celquat SC-240 | 38.6 | — |  |
| Polymer JR-400 | — | 31 |  |
| BHT | 1.95 | 1.95 |  |
| Kathon CG | 1.3 | 1.3 | — |
|  | 1347.97 | 1307.9 |  |
| Mw as determined by SEC | 90,000 | 179,000 | 46,500 |

Example 8a

Biochemical Process Coupled with Chemical Process Using an Oxidative Reagent

A product of 10% total solids, molecular weight (Mw) of 45,000-65,000 Dalton, was prepared using the following process. The product prepared also had aldehyde functional groups on the low molecular weight cationic guar.

1) 700 g of tap water was heated to 50° C. in a glass reactor equipped with an overhead mixer.

2) 282 g of washed wet cationic guar splits were added to the water to form a slurry.

3) 300 mg of mannanase (from ChemGen Corp., Rockville, Md.) were added to the cationic guar splits slurry once the pH was adjusted with an acid to below 9.0 but before it reaches pH 7.5. After 30 minutes at basic pH of 9.0-8.0, the pH was incrementally reduced to pH 5.0-5.5 with an acid.

4) Once the cationic guar splits slurry fully hydrated and a thick apple sauce-like suspension started to thin down, 13.6 g of 30% $H_2O_2$ (4,000 ppm or 0.40% in the guar suspension) were added to the cationic guar splits suspension.

5) The temperature was raised to 90° C.

6) Once the in-process viscosity of the suspension decreased to 230-280 cps, the heating of the reactor was stopped and 0.1-0.5 g of sodium metabisulfite was added to instantly eliminate residual $H_2O_2$ as measured by test strip E-M Quant® peroxide test 7) The $H_2O_2$ level was verified as being zero using the test strip.

8) 1 g of Kathon CG (0.1%) solution was added to the final product as a preservative.

Example 8b

Biochemical Process Coupled with Chemical Process Using an Oxidative Reagent

Preparation of Lower Molecular Liquid Polymer from High Molecular Weight PRECURSOR 3 Cationic Guar by Enzyme Degradation Followed by Peroxide Degradation.

Experiment 8b(1)

933 g of water were heated to about 50-55° C. In a separate container 0.05 g of mannanse enzyme was premixed with water. The premix was added to the heated water while mixing. Next, 56.5 grams of high molecular weight, 999,145 Dalton PRECURSOR 3 polymer with cationic DS of about 0.9 were added while mixing. The polymer slurry temperature was raised to about 90° C. over about 90 minutes.

Next 2.22 g of 1.0% $H_2O_2$ were added and mixed for 45 minutes. Next 0.19 g of sodium meta bisulfite was added and cooled. 10 g of Germaben® II preservative and make-up water were added to bring the batch size to 1000 g. The polymer molecular weight was 963759 Dalton.

Experiment 8b(2)

In another experiment 933 g of water were heated to about 45-55° C. In a separate container 0.10 g of mannanse enzyme was premixed with water. The premix was added to the heated water while mixing. Next, 56.5 grams of high molecular weight, 999,145 Dalton PRECURSOR 3 polymer with cationic DS of about 0.9 were added while mixing. The pH of the slurry was about 8.2. The slurry pH was lowered to about 6.1 with HCl. The slurry was mixed for about 50 minutes and a sample of the polymer solution was taken for analysis. Molecular weight of the polymer was about 862,000 Dalton. The sample was tested for aldehyde level with M Quant Formaldehyde Test strips available from EM Science of Gibbstown, N.J. The polymer sample had 0 ppm formaldehyde. Next, the polymer solution was raised to about 90° C. and 4.44 grams of 1.0% peroxide solution were added. The reaction was stopped with 0.2 g of sodium metabisulfite. Next, 17.6 g of 1.0% hydrogen peroxide solution were added and stirred for about 60 minutes at about 90° C. Next, 0.34 g of sodium meta bisulfite was added and cooled. The solution was preserved with 0.5% Phenoxetol® and 0.18% Nipasept® Sodium preservatives. Both preservatives are available from Clariant Corporation. This sample had 10 ppm of aldehyde as per the strip test. The sample had weight average molecular weight of 293,000 Dalton.

Example 8c

Biochemical Process Coupled with Chemical Process Using an Oxidative Reagent

Preparation of Lower Molecular Weight Liquid Polymer from High Molecular Weight N-Hance® 3000 Cationic Guar by Peroxide Degradation Followed by Enzymatic Degradation N-Hance 3000 polymer used in this example had cationic DS of about 0.06 and weight average molecular weight 923,655 Dalton. 929 g of water were heated to about 90° C. in a silicone oil bath. 10.5 grams of 1.0% active $H_2O_2$ was added to the heated water. Next, 50 grams of N-Hance® 3000 polymer were added the water-peroxide mix and was maintained for about 110 minutes at 80 to 90° C. 0.19 grams of sodium meta bisulfite was added and mixed for an additional 10 minute and cooled. The pH was adjusted to 6.5 with hydrochloric acid. 10 grams of Germaben® II preservative and make-up water were added to adjust total batch size to 1000 g and mixed. This produced a 1000 gram batch with 5% polymer. The final product had a weight average molecular weight of 418,000 Dalton.

815 g of the above peroxide degraded polymer solution sample was heated to about 50-55° C. In a separate container 0.05 g of mannase enzyme was premixed with water. The premix was added to the polymer solution while mixing. The polymer solution temperature was raised to about 92° C. over about 70 minutes. The sample was removed from the oil bath and allowed to cool while mixing. 8 g of Germaben® II preservative and make-up water were added to bring the batch size to 815 g. The polymer weight average molecular weight was 131,308 Dalton.

Example 8d

Biochemical Process without an Oxidative Reagent

Preparation of Lower Molecular Weight Liquid Polymer from High Molecular Weight Cationic Guar by Enzyme Degradation The procedure in steps 1-3 of Example 8a was followed. Once the desired viscosity was reached, the temperature was raised to 90° C. to denature the enzyme and stop the reaction. The mixture was allowed to cool to ambient temperature, and 0.1% Kathon CG preservative was added to the reaction mixture. The weight average molecular weight of the product was 67,000 Dalton. The sample contained no aldehyde content as determined by the indirect iodometric titration method.

Example 9

Biochemical Process Coupled with Biochemical Oxidation

A product of 10% total solids, with Mw of 40,000 was prepared. The product had aldehyde groups on the low molecular weight cationic guar. The procedure was as follows:

1) 700 g of tap water at 25° C. were placed in a glass reactor equipped with an overhead mixer.

2) 282 g of washed wet cationic guar splits with about 60-65% moisture were added to the reactor to form a suspension while stirring with the overhead mixer.

3) Carefully but quickly, fumaric acid was added to the reactor for adjusting the pH to 6.5-7.5.

4) 300 mg of mannanase were added to the guar splits suspension.

5) Then, the suspension was sparged with air at 0.1-0.3 volume of air per volume of the suspension per minute.

6) Next, 6,000 international units of galactose oxidase (from Hercules Incorporated, Wilmington Del.), 60,000 international units of catalase (Terminox Ultra 50L product from NovoZymes, Franklintown, N.C.), and 1,500 units of peroxidase (NS51004, also from NovoZymes) were added to the above suspension.

7) The reaction was permitted to continue for 1-3 hours depending on the desired molecular weight and the level of oxidation of the final product.

8) At the end of the reaction, the pH was adjusted to 4.0, then the reactor was heated up to 90° C. and held for 30 min. to deactivate the enzymes.

9) 1 g of Kathon CG (0.1%) solution was added to the final product as a preservative.

The aldehyde content of this sample as measured by the change in the ratio of galactose/mannose is 0.4 meq/gram.

Examples 10-15

Conditioning Shampoo Examples

Performance of Cationic Oxidized Polysaccharides of the Invention in Conditioning Shampoos In a shampoo formulation, conditioning agent, cationic guar or cationic hydroxyethylcellulose, was added to improve detangling of both wet hair and dry hair, as demonstrated by reduction in the energy to comb wet and dry hair. The results in Table 7, Examples 11, 12 and 14 demonstrate that cationic, oxidized guars and cationic, oxidized hydroxyethylcellulose materials of the invention improve detangling of both wet and dry hair, when compared with the shampoo containing no polymer in Example 10. In Example 11 and 12, a shampoo prepared with cationic, oxidized guars of low and medium molecular weight, prepared according to the process described as in experiment U in Table 5, gave wet comb energy reduction for bleached medium brown European hair of 62% and 51%, respectively, and dry comb energy reductions of 35% and 22%, respectively. The wet and dry comb energy reductions achieved by the polymers of this invention are equivalent or better than the corresponding performance of the high molecular weight cationic guar in comparative Example 13. The wet and dry comb energy reduction of the polymers of this invention in Examples 11 and 12 are also improved over the performance of the shampoo containing no polymer in Example 10, which was 9% and 7%, respectively.

added mixed 15 minutes. The pH value of the shampoo was checked and, when necessary, the pH was re-adjusted to between 5.0 and 5.5. The shampoo was mixed 15 minutes when adjusted.

TABLE 7

| Ingredients | Example 10 | Example 11 | Example 12 | Example 13 | Example 14 | Example 15 |
|---|---|---|---|---|---|---|
| Deionized water | 48.5 | 48.5 | 48.5 | 48.5 | 48.5 | 48.5 |
| HPMC60SH4000 | 0.5 | 0.5 | 0.5 | 0.5 | 0.0 | 0.0 |
| N-Hance ® 3215 | 0.0 | 0.0 | 0.0 | 0.5 | 0.0 | 0.0 |
| Cationic guar of Invention | 0.0 | 0.5 | 0.5 | 0.0 | 0.0 | 0.0 |
| Cationic Hydroxyethyl-cellulose of the invention | 0.0 | 0.0 | 0.0 | 0.0 | 0.2 | 0.0 |
| Cationic Guar of Example 8D | 0.0 | 0.0 | 0.0 | 0.0 | 0.0 | 0.5 |
| Amphosol ® CA | 12 | 12 | 12 | 12 | 12 | 12 |
| Rhodapex ® ES STD | 35 | 35 | 35 | 35 | 35 | 35 |
| 10 wt % Sodium Chloride | 4 | 4 | 4 | 4 | 4 | 4 |
| Glydant ® | 0.5 | 0.5 | 0.5 | 0.5 | 0.5 | 0.5 |
| Citric Acid (5%) | Adjust pH | Adjust pH | Adjust pH | Adjust pH | Adjust pH | Adjust pH |
| Water | q.s to 100 | q.s to 100 | q.s to 100 | q.s to 100 | q.s to 100 | q.s to 100 |
| Total Shampoo | 100 | 100 | 100 | 100 | 100 | 100 |
| Appearance | Hazy, | V. Hazy, some gels | Hazy, some gels | translucent | Clear | Very Hazy, sediment |
| PH | 5.4 | 5.5 | 5.3 | 5.6 | 5.41 | 5.41 |
| Reduction in Wet Comb Energy (%) | −9 | 62 | 51 | 52 | 45 | 51 |
| Reduction in Dry Comb Energy (%) | 7 | 35 | 22 | 28 | 16 | 8 |
| Mw | — | 50200 | 197000 | 1200000 | 45,600 | 67200 |
| Cationic DS | — | 0.18 | 0.18 | 0.18 | 0.3 | 0.18 |

Example 14 demonstrates that the polymer of this invention derived from a cationic hydroxyethylcellulose polymer, prepared according to the procedure described in experiment AF in Example 7, Table 6, also gave better wet and dry combing performance than the no polymer control Example 10.

Example 15 is included as a comparative example for a low molecular weight cationic guar prepared by biochemical degradation, without an oxidative treatment, as described in Example 8d. Note, that this polymer gave improved wet and dry comb performance over the no polymer control example in Example 10; however, the shampoo developed a sediment over time.

In Table 7, Examples 10-14, conditioning shampoos were prepared using the following ingredients and procedures.

Phase 1 Water was heated in a vessel to 80-90° C. and HPMC was added while mixing. Cationic, oxidized polysaccharide was added to the heated water while mixing at ~60-65° C. The mixture was allowed to cool to 25-35° C. while mixing.
  Citric acid was added to the cooled mixture to lower the pH to 5.00 to 6.00
  The mixture was then stirred until dissolved, about one hour.

Phase 2 Rhodapex ES STD product was weighed into a separate tarred beaker.
  Phase 1 was added to Phase 2 while mixing.
  The pH was re-adjusted to 5.0 to 5.5 with citric acid.
  The mixture was stirred for 30-60 minutes until homogeneous.

Phase 3 Amphosol CA product was added to the combined Phases 1 and 2 while mixing and stirred additionally for five-minutes after completion of mixing.
  Mixing was continued until homogeneous.

Phase 4 Sodium chloride solution (10 wt %) was added to Phase 3 and stirred for 5 minutes. Glydant product was (1) Amphosol CA, 30% Active (Stepan Chemicals, Chicago, Ill.)

(2) Rhodapex ES STD, 30% active (Rhodia Incorporated, Cranberry, N.J.))

(3) Glydant™ 55% active, (Lonza, Fair Lawn, N.J.)

(4) Hydroxypropylmethylcellulose—HPMC60SH4000 (Shin Etsu, Tokyo, Japan).

Examples 16-20

Effect of Polymer MW on Formulation Viscosity

In a shampoo formulation, conditioning agent, cationic guar, was added to improve detangling of both wet hair and dry hair. The current commercially available cationic guar can only be used at very low level, since it has a significant impact on the viscosity of the shampoo product. In examples 16-20, in Table 8, shampoo was made 1) without the cationic guar, 2) with 0.2% and 1.5% commercially available N-Hance® 3215 cationic guar, and 3) with 1.5% cationic, oxidized guar product of this invention.

Shampoo preparation: A container of water was heated to 70° C. by placing in a 70° C. water-bath. Benecel® product was sifted into the heated water while mixing. Next, commercial N-Hance® 3215 product or polymer of this invention was added to the container while mixing. The solution that was formed was cooled to about 40° C., while mixing. The remainder of the ingredients of the shampoo was added to the container in the order listed. The shampoo pH was adjusted to about pH 5.5. The shampoo was cooled to room temperature while mixing.

The product of this invention used in Examples 17 and 19, in Table 8, was an aqueous solution with about 10% solids and weight average molecular weight of about 42,000 Dalton prepared according to the procedure used in experiment Y in Table 5. In comparison the commercial N-Hance® 3215 product is a dry polymer with molecular weight of about 1 million. Because of its high molecular weight it has a significant effect on the viscosity of the conditioning shampoo. In Table 8, Example 16 shampoo was made without a conditioning agent. It has a Brookfield viscosity of about 3,540 cps. In Example 18, same shampoo made with 1.5% N-Hance 3215 product has Brookfield LVT viscosity of 193,000 cps. At such a high viscosity it is not only difficult for a formulator to fill the shampoo bottles but it is also very difficult to dispense by a consumer. Most of the commercial shampoos are less than 10,000 cps in viscosity. Even at 0.2% N-Hance® 3215 product in Example 20 the shampoo viscosity was 13,600 cps. However, the product of this invention (Example 17) was used at 1.5% active and maintained a shampoo viscosity of 9,180 cps. When the polymer of the invention (Example 19) was used at 0.2%, the shampoo viscosity was 8,300 cps. All viscosities were measured at 12 rpm, 25° C., using Brookfield viscometer model LVT.

The conditioning shampoo was tested for its combing performance on a mildly bleached European virgin hair. A 12-inch hair tress weighing around 5 grams was used. In this study, reduction in combing energy was measured. Reduction in combing energy is an indirect measurement of conditioning performance of a polymer. As shown in Example 16, if conditioning polymer is not used in the shampoo, it takes more force to comb hair. A negative combing energy is an indication of hair entanglement and needs higher force or energy to comb the hair. At the polymer level of 0.2%, the polymer of this invention (Example 19, Table 8) and the commercial polymer (Example 20, Table 8) provided about the same level of reduction in wet combing energy, 15.8% and 17.1%, respectively. However, the polymer of this invention (Example 17) at 1.5% polymer level provided significantly higher reduction in wet combing, 53.7%. A shampoo with 1.5% commercial N-Hance® 3215 product was not tested, since it had viscosity significantly outside the shampoo viscosity range (Example 18).

TABLE 8

| Ingredients | Example 16 | Example 17 | Example 18 | Example 19 | Example 20A | Example 20B |
|---|---|---|---|---|---|---|
| Deionized water | 51.6 | 51.6 | 51.6 | 51.6 | 51.6 | 51.6 |
| Benecel ® MP943 | 0.6 | 0.6 | 0.6 | 0.6 | 0.6 | 0.6 |
| N-Hance ® 3215 | 0.0 | 0.0 | 1.5 | 0.0 | 0.2 | 0.5 |
| Cationic guar of Invention Experiment Y, Table 5 | 0.0 | 13.64(1.5% active) | 0.0 | 1.82 (0.2% active) | 0.0 | 0.0 |
| Stepanol ® AM | 27.5 | 27.5 | 27.5 | 27.5 | 27.5 | 27.5 |
| Miranol ® C2M | 6.9 | 6.9 | 6.9 | 6.9 | 6.9 | 6.9 |
| Steol CS330 | 11.4 | 11.4 | 11.4 | 11.4 | 11.4 | 11.4 |
| Germaben ® II | 0.5 | 0.5 | 0.5 | 0.5 | 0.5 | 0.5 |
| Citric Acid (5%) | Adjust pH | Adjust pH | Adjust pH | Adjust pH | Adjust pH | Adjust pH |
| Water | q.s to 100 | q.s to 100 | q.s to 100 | q.s to 100 | q.s to 100 | q.s to 100 |
| Total Shampoo | 100 | 100 | 100 | 100 | 100 | 100 |
| Viscosity | 3540 | 9180 | 193800 | 8300 | 13600 | 23250 |
| PH | 5.4 | 5.5 | 5.3 | 5.6 | 5.41 | 5.5 |
| % T 600 nm | | | | | | |
| Reduction in Wet Comb Energy (%) | −1.1 | 53.7 | Not Tested | 15.8 | 17.1 | |
| Reduction in Dry Comb Energy (%) | −28.0 | 7.4 | Not tested | 33.4 | 9.2 | |
| Mw | — | 42030 | 1087074 | 42030 | 1087074 | 1087074 |
| Cationic DS | — | 0.23 | 0.26 | 0.23 | 0.26 | 0.26 |

(1) Benecel ® MP943 — Hydroxypropylmethylcellulose — Aqualon, Wilmington, DE
(2) N-Hance ® 3215 — Guar hydroxypropyl Trimmonium chloride — Aqualon, Wilmington, DE
(3) Cationic Guar Of invention (11.0% active) — Guar hydroxypropyl trimonium chloride — Aqualon, Wilmington, DE
(4) Stepanol ® AM — Ammonium Lauryl Sulfate — Stepan Co. Northfield, Il
(5) Miranol ® C2M Conc. — NP Disodium Cocoampho diacetate — Stepan Co. Northfield, Il
(6) Steol ® CS 330 — Sodium laureth sulfate — Stepan Co. Northfield, Il
(7) Germaben ® II — Preservative — ISP Wayne, NJ Examples 21-32

Demonstration of Improved Performance at Higher Polymer Concentrations without Affecting Viscosity of Shampoo In Table 9, the effect of concentration of polymer of this invention on wet combing performance of shampoo is shown. The higher the reductions in wet combing energy of hair, the greater the conditioning effects imparted by the conditioning polymer. Based on the wet combing data in Examples 21-25, at least 0.8% active polymer is desired for maximum wet combing performance. With commercially available high molecular weight cationic guars, such as N-Hance® 3215 product, the shampoo viscosity was 13,600 cps at 0.2% polymer level (Example 20A of Table 8) and at 0.5% polymer level it is 23,250 cps (Example 20B of Table 8). Both these viscosities are considered at the edge of the desired viscosity range for commercial shampoos, as shown in Examples 26-30 in Table 10. However, with the polymer of this invention, the shampoo viscosity was below 10,000 cps even at a polymer level as high as 1.5%, Examples 17 of Table 8 and 25 of Table 9. Comparison of the viscosities for the shampoos in Examples 31 and 32 in Table 11 further demonstrated the effect of the polymer of the present invention on conditioning performance on hair without the effect on shampoo viscosity, even for a guar having a higher cationic DS. The polymer in Example 32 was prepared according to the procedure in Experiment Z, Table 5, Example 6. The shampoo was made using the procedure described for shampoos in Table 8. The shampoo viscosity was about 11,000 cps with 1.5% polymer of this invention, Example 32, compared to 32,000 cps for high molecular weight polymer, Example 31. The polymer of the present invention in Example 32 had slightly better wet combing performance.

These results demonstrate that the polymer of the present invention allows the formulator to add extra conditioning without significantly increasing the shampoo viscosity.

TABLE 9

| Ingredients | Example 21 | Example 22 | Example 23 | Example 24 | Example 25 |
|---|---|---|---|---|---|
| Deionized water | 51.3 | 48.6 | 45.8 | 44.0 | 39.5 |
| Benecel ® 943 | 0.6 | 0.6 | 0.6 | 0.6 | 0.6 |
| N-Hance ® 3215 | 0.0 | 0.0 | 0.0 | 0.0 | 0.0 |
| Cationic guar of Invention Table 5, Experiment Y | 1.82 (0.2% active) | 4.55 (0.5% active) | 7.27 (0.8% active) | 9.10 (1.0% active) | 13.64 (1.5% active) |
| Stepanol ® AM | 27.5 | 27.5 | 27.5 | 27.5 | 27.5 |
| Miranol C2M | 6.9 | 6.9 | 6.9 | 6.9 | 6.9 |
| Steol ® CS330 | 11.4 | 11.4 | 11.4 | 11.4 | 11.4 |
| Germaben ® II | 0.5 | 0.5 | 0.5 | 0.5 | 0.5 |
| Citric Acid (5%) | Adjust pH | Adjust pH | Adjust pH | Adjust pH | Adjust pH |
| Water | q.s to 100 | q.s to 100 | q.s to 100 | q.s to 100 | q.s to 100 |
| Total Shampoo | 100 | 100 | 100 | 100 | 100 |
| Viscosity (cps) | 8300 | 9450 | 7600 | 6250 | 7700 |
| PH | 5.6 | 5.4 | 5.7 | 5.5 | 5.4 |
| % T600 nm | 83.8 | 71.6 | 62 | 57.7 | 43.5 |
| Reduction in Wet Comb Energy (%) | 15.8 | 33.6 | 45.5 | 39.7 | 40.9 |
| Reduction in Dry Comb Energy (%) | 33.4 | 14.9 | 25.3 | 11.7 | 5.8 |
| Mw | 42030 | 42030 | 42030 | 42030 | 42030 |
| Cationic DSDS | 0.23 | 0.23 | 0.23 | 0.23 | 0.23 |

TABLE 10

| Ingredients | Example 26 | Example 27 | Example 28 | Example 29 | Example 30 |
|---|---|---|---|---|---|
| | Clairol ® Herbal Essences ® Shampoo | Panteen ® Pro-V ® Shampoo | Pantene ® Pro-V ® Shampoo plus Conditioner | Finesse Plus ® Silk Protein | Johnson's ® Baby Shampoo Detangling Formula |
| Brookfield LVT Viscosity at 12 rpm | 7630 cps | 7250 cps | 12300 cps | 2080 cps | 1740 cps |

TABLE 11

| Ingredients | Example 31 | Example 32 |
|---|---|---|
| Deionized water | 51.6 | 25.17 |
| Benecel ® 943 | 0.6 | 0.6 |
| PRECURSOR 1 | 1.5 | 0.0 |
| Cationic guar of Invention Table 5, Experiment AA Polymer | 0.0 | 27.93 (1.5% active) |
| Stepanol ® AM | 27.5 | 27.5 |
| Miranol ® C2M | 6.9 | 6.9 |
| Steol ® CS330 | 11.4 | 11.4 |
| Germaben ® II | 0.5 | 0.5 |
| Citric Acid (5%) | Adjust pH | Adjust pH |
| Water | q.s to 100 | q.s to 100 |
| Total Shampoo | 100 | 100 |
| Viscosity (cps) | 32500 | 11250 |
| PH | 5.3 | 5.2 |
| Polymer | | |
| Mw | 1,200,000 | 27,900 |
| Cationic DS | 0.48 | 0.52 |
| % Reduction Wet Combing | 17.1 | 24.4 |

| (1) | Benecel® MP943 | Hydroxypropyl-methylcellulose | Aqualon, Wilm., DE. |
| --- | --- | --- | --- |
| (2) | PRECURSOR 1 | Gar hydroxypropyl trimonium chloride | Aqualon, Wilm., DE |
| (3) | Experiment AA Polymer of invention (5.4% active) | Guar hydroxypropyl trimonium chloride | Aqualon, Wilm., DE |
| (4) | Stepanol® AM | Ammonium Lauryl sulfate | Stepan Co. Northfield, IL |
| (5) | Miranol® C2M Conc. NP | Disodium Cocoamppho diacetate | Stepan Co. Northfield, IL |
| (6) | Steol® CS 330 | Sodium laureth sulfate | Stepan Co. Northfield, Il |
| (7) | Germaben® II | Preservative | ISP Wayne, NJ |

The shampoo was made using the procedure described for Table 8. All viscosities were measured at 12 rpm, 25° C., using Brookfield viscometer model LVT.

Examples 33-37

Shower Gels

Comparative Effect of Increasing Polymer Concentration on Shower Gel Viscosity and Lather Stability for Polymer of Invention vs. Commercial Cationic Guar The conditioning shower gel in Table 12 was made first dispersing Benecel® MP943 product in water. Next N-Hance® 3196 product or the cationic polymer of this invention was added. And then the remainder of the ingredients of the shower gel were added in the order listed, while mixing well between each addition. Once all the ingredients are well mixed, shower gel pH was lowered to between 5.0 and 6.0 with citric acid. All viscosities were measured at 12 rpm, 25° C. using Brookfield LVT viscometer.

Again, in the shower gel the commercial N-Hance® 3196 polymer could not be added at 1.5% without a very significant increase in the viscosity, Example 34, Table 12. The viscosity of the conditioning shower gel with commercial N-Hance 3196 polymer was 42,700 cps at 12 rpm as compared to a shower gel without the polymer having viscosity of only 460 cps, Example 33. With the polymer of the invention at a concentration of 1.5%, the viscosity was only 3,380 cps, Example 35. Examples 36, 37, and 34 show the effect of commercial N-Hance® 3196 polymer on shower gel viscosity when compared to Example 33 without the conditioning product polymer. The viscosity measurements were made at 12 rpm, 25° C. using Brookfield LVT viscometer.

The lather drainage was measured using the method described below. Lather drainage time is an indirect method of measuring lather stability. A longer drainage time is an indication of more stable and richer lather. A consumer perceives more stable lather as positive. The lather drainage time was more than double for the shower gel with the polymer of this invention (Example 35) than that of shower gel without the polymer of the invention, Example 33. In Example 37, with 0.5% of commercial N-Hance® 3196 cationic guar, almost the same viscosity was reached as with the polymer of this invention (Example 35) but the polymer of the present invention had over 20% higher lather stability.

Description of Lather Test Equipment/Method

Lather Test: This method was used for measuring the lather drainage time of a diluted shower gel to determine the influence of conditioning polymer on lather quality. Long drainage time indicate a rich, dense lather with good stability.

Equipment:

Waring® Blender Model #7012 or 34BL97 or equivalent.

Funnel, preferably plastic; 6" diameter, ⅞" ID neck, 5¼" high, with a horizontal wire 2" from the top. U.S.A. Standard Testing Sieve NO. 20, 7 inch in diameter. Stopwatch.

Procedure:

1000 g of a diluted shower gel solution was prepared in a beaker

| | |
| --- | --- |
| Shower Gel | 66.45 g |
| Deionized Water | 933.55 g |
| Total | 1000.00 g |

Next 200 grams of diluted solution was weighed in an 8 oz jar. Three jars with 200 grams of diluted shower gel were prepared. The jars were then placed in a water bath set to 40° C. temperature for two hours. The jars were fully immersed. The lather drainage test was run as follow. A total of 3 measurements were made for each formulation.

200 g of diluted shower gel was poured into a clean, dry Waring blender glass vessel. The shower gel was whipped to form a foam on the highest speed for exactly 1 minute while covered. Immediately the foam was poured into a clean, dry funnel standing on a 20-mesh screen over a beaker. The foam was poured from the blender for exactly 15 seconds. Attempt was made to get as much foam as possible into the funnel without overflowing. At 15 seconds, stopped pouring the foam. The total time needed for the foam to drain (including the 15 seconds of pour time) so that the wire was no longer covered by foam or liquid was noted. The test was run in triplicate. Results were reported in seconds in Table 12.

REFERENCES (1) Evaluation of the foaming Capacity in shampoos: Efficacy of various Experimental Methods by F. J. Domingo Campos, R. M. Druguet Tantina, Cosmetic & toiletries Page 121-130, Vol. 98, September 1983
(2) The Lathering Potential of Surfactants—Simplified Approach to measurement by J. Roger Hart and Mark T. DeGeorge. J. Soc. Cosmet. Chem., 31, 223-236 September/October 1980

Conditioning Shower Gel

TABLE 12

| Ingredients | Example 33 | Example 34 | Example 35 | Example 36 | Example 37 |
| --- | --- | --- | --- | --- | --- |
| Deionized water | 46.19 | 44.69 | 19.36 | 45.99 | 45.69 |
| Benecel® 943 | 1.0 | 1.0 | 1.0 | 1.0 | 1.0 |
| N-Hance® 3196 | 0.0 | 1.5 | 0.0 | 0.2 | 0.5 |

TABLE 12-continued

| Ingredients | Example 33 | Example 34 | Example 35 | Example 36 | Example 37 |
|---|---|---|---|---|---|
| Cationic guar of Invention | 0.0 | 0.0 | 26.83 (1.5% active) | 0.0 | 0.0 |
| Steol ® CS330 | 23.06 | 23.06 | 23.06 | 23.06 | 23.06 |
| Stepan ® Mild SL3 BA | 11.8 | 11.8 | 11.8 | 11.8 | 11.8 |
| Miranol ® C2M | 6.0 | 6.0 | 6.0 | 6.0 | 6.0 |
| Crodasinic ® LS-30 | 7.25 | 7.25 | 7.25 | 7.25 | 7.25 |
| Propylene glycol | 2.0 | 2.0 | 2.0 | 2.0 | 2.0 |
| Euperlan ® PK3000 | 2.0 | 2.0 | 2.0 | 2.0 | 2.0 |
| Disodium EDTA | 0.1 | 0.1 | 0.1 | 0.1 | 0.1 |
| Phenonip ® | 0.6 | 0.6 | 0.6 | 0.6 | 0.6 |
| Citric Acid (5%) | Adjust pH | Adjust pH | Adjust pH | Adjust pH | Adjust pH |
| Water | q.s to 100 | q.s to 100 | q.s to 100 | q.s to 100 | q.s to 100 |
| Total Shower gel | 100 | 100 | 100 | 100 | 100 |
| Viscosity (cps) | 458 | 42700 | 3380 | 1822 | 5920 |
| pH | 5.6 | 5.8 | 5.5 | 5.5 | 5.5 |
| Lather drainage time (seconds) | 53.3 seconds | | 117.3 second | | 95.3 seconds |
| Polymer | | | | | |
| Mw | | 1,050,000 | 550,000 | 1,050,000 | 1,050,000 |
| Cationic DS | | 0.17 | 0.14 | 0.17 | 0.17 |

| | | | |
|---|---|---|---|
| (1) | Benecel ® MP943 | Hydroxypropyl-methylcellulose | Aqualon, Wilm., DE |
| (2) | N-Hance ® 3196 | Gar hydroxypropyl trimmonium chloride | Aqualon, Wilm., DE |
| (3) | Cat guar of invention (5.6% active) | Guar hydroxypropyl trimmonium chloride | Aqualon, Wilm., DE |
| (4) | Stepan ® Mild SL3 BA | Disodium laureth Sulfosuccinate | Stepan Co. Northfield, IL |
| (5) | Miranol ® C2M Conc. NP | Disodium Cocoamppho diacetate | Stepan Co. Northfield, IL |
| (6) | Steol ® CS 330 | Sodium laureth sulfate | Stepan Co. Northfield, IL |
| (7) | Phenonip | Preservative | Clariant, Mt. Holly, NC |
| (8) | Crodasinic ® LS-3 | Sodium Lauryl Sarcosinate | Croda, Inc Parsippany, NJ |
| (9) | Propylene glycol, USP | | EM Industries Gibbstown, NJ |
| (10) | Euperlan ® PK3000 | | Cognis, Amber, PA |
| (11) | Disodium EDTA | | VWR |

The polymer of the Invention in Example 35 of Table 12 was prepared by a method similar to the method described for experiment Z, in Table 5, Example 6, where N-Hance 3205 cationic guar was used in place of PRECURSOR 2 cationic guar. The molecular weight of the final product was 550,000 Dalton, reduced from a molecular weight of 1,050,000 Dalton measured for the starting N-Hance 3205 cationic guar.

Examples 38-42

Again, in the shower gel commercial cationic hydroxypropyl guar, Jaguar® C 162 polymer could not be added at 2.0% without a very significant increase in the viscosity, Example 39, Table 13. Viscosity of conditioning shower gel with commercial Jaguar® C162 was 41,400 cps at 12 rpm as compared to shower gel without the polymer having viscosity of only 555 cps. With the polymer of this invention, viscosity was only 3,320 cps, Example 40 with 2.0% active polymer. The viscosity measurements were made at 12 rpm, 25° C. using Brookfield LVT viscometer. The commercial Jaguar® C162 product was also tested at 0.2% and 0.5% active level, Examples 41 and 42. At 0.5% level (Example 42) it reached the same viscosity as the formulation with 2.0% polymer of this invention, Example 40. The lather stability was measured using the method previously described. Lather drainage time for the shower gel in Example 40, the polymer of the invention, was more than double than that of shower gel without the polymer of invention (Example 38). The longer the drainage time, the more stable the lather.

The polymer of Invention described in Example 40, Table 13 was made by a procedure similar to the procedure used for experiment Z in Example 6, Table 5, with substitution of Jaguar® C162 cationic hydroxypropyl guar for PRECURSOR 2 cationic guar. The product had a molecular weight of 555,532 Dalton, reduced from a starting molecular weight of 1,080,000 Dalton for the starting Jaguar C162 cationic hydroxypropyl guar.

Comparative Effect of Polymer of Invention vs.
Commercial Cationic Hydroxypropyl Guar on
Shower Gel Viscosity and Lather Stability

TABLE 13

| Ingredients | Example 38 | Example 39 | Example 40 | Example 41 | Example 42 |
|---|---|---|---|---|---|
| Deionized water | 46.19 | 44.69 | 26.19 | 45.99 | 45.69 |
| Benecel ® 943 | 1.0 | 1.0 | 1.0 | 1.0 | 1.0 |
| Jaguar ® C162 | 0.0 | 2.00 | 0.0 | 0.2 | 0.5 |

TABLE 13-continued

| Ingredients | Example 38 | Example 39 | Example 40 | Example 41 | Example 42 |
|---|---|---|---|---|---|
| Cationic guar of Invention From C162 | 0.0 | 0.0 | 20.00 (10.0% active) | 0.00 | 0.00 |
| Steol ® CS330 | 23.06 | 23.06 | 23.06 | 23.06 | 23.06 |
| Stepan ® Mild SL3 BA | 11.8 | 11.8 | 11.8 | 11.8 | 11.8 |
| Miranol ® C2M | 6.0 | 6.0 | 6.0 | 6.0 | 6.0 |
| Crodasinic ® LS-30 | 7.25 | 7.25 | 7.25 | 7.25 | 7.25 |
| Propylene glycol | 2.0 | 2.0 | 2.0 | 2.0 | 2.0 |
| Euperlan ® PK3000 | 2.0 | 2.0 | 2.0 | 2.0 | 2.0 |
| Disodium EDTA | 0.1 | 0.1 | 0.1 | 0.1 | 0.1 |
| Phenonip ® | 0.6 | 0.6 | 0.6 | 0.6 | 0.6 |
| Citric Acid (5%) | Adjust pH | Adjust pH | Adjust pH | Adjust pH | Adjust pH |
| Water | q.s to 100 | q.s to 100 | q.s to 100 | q.s to 100 | q.s to 100 |
| Total | 100 | 100 | 100 | 100 | 100 |
| Shower gel | | | | | |
| Viscosity (cps) | 555 | 41400 | 3320 | 1390 | 3180 |
| pH | 5.6 | 5.6 | 5.8 | 5.2 | 5.4 |
| Lather drainage time (seconds) | 53.7 seconds | | 94.7 second | | 92 seconds |
| Polymer | | | | | |
| Mw | | 1080880 | 555532 | 1080880 | 1080880 |
| Cationic DS | | 0.1 | 0.1 | 0.1 | 0.1 |

| | | | |
|---|---|---|---|
| (1) | Benecel ® MP943 | Hydroxypropyl-methylcellulose | Aqualon, Wilm., DE |
| (2) | Jaguar ® C162 | hydroxypropyl Gar hydroxypropyl trimmonium chloride | Rhodia, |
| (3) | Cat guar of invention (10% active) | hydroxypropyl Guar hydroxypropyl trimmonium chloride | Aqualon, Wilm., DE |
| (4) | Stepan ® Mild SL3 BA | Disodium laureth Sulfosuccinate | Stepan Co. Northfield, Il |
| (5) | Miranol ® C2M Conc. NP | Disodium Cocoampphodiacetate | Stepan Co. Northfield, Il |
| (6) | Steol ® CS 330 | Sodium laureth sulfate | Stepan Co. Northfield, Il |
| (7) | Phenonip ® | Preservative | Clariant, Mt. Holly, NC |
| (8) | Crodasinic ® LS-3 | Sodium Lauryl Sarcosinate | Croda, Inc, Parsippany, NJ |
| (9) | Propylene glycol, USP | | M Industries, Gibbstown, NJ |
| (10) | Euperlan ® PK3000 | | Cognis, Amber, PA |
| (11) | Disodium EDTA | | VWR |

Examples 43-47

Comparative Examples of the Effect of Polymer Concentration on Liquid Soap Viscosity and Lather Stability for High MW Cationic Guar vs. Polymer of the Invention Table 14 show the effect of concentration of commercial N-Hance® 3198 cationic guar on the viscosity of liquid soap and its lather stability. The viscosity increase from 123 cps for liquid soap with no polymer (Example 43) to 23,400 cps with 1.5% of commercial N-Hance 3198 product (Example 46). The liquid soap can become difficult to dispense at such a high viscosity. With the polymer of the invention (Example 47) at 1.5% active formulation viscosity was only 315 cps. To maintain such a low viscosity the commercial polymer could only be used at 0.2% active level (Example 44). However, at this level liquid soap had inferior lather stability. The lather stability was only about 30 seconds compared to about 71 seconds with polymer of this invention (Example 47).

Liquid Soap Preparation

Natrosol hydroxyethyl cellulose was dispersed in water while mixing. Next cationic guar (commercial N-Hance® 3198 or polymer of this invention) was added while mixing. The Ammonyx® 4002, Bioterge® AS40 and Emerest® ingredients were added in the order listed while mixing. The batch was mixed in an 80° C. water-bath until the Emerest® ingredient dissolved; Next, the batch was removed from the water-bath and allowed to cool while mixing. The remaining ingredients were added while the batch was cooling to room temperature.

TABLE 14

| Ingredients | Example 43 | Example 44 | Example 45 | Example 46 | Example 47 |
|---|---|---|---|---|---|
| Deionized water | 75.73 | 75.53 | 75.23 | 74.23 | 49.69 |
| Natrosol ® 250MR | 0.80 | 0.80 | 0.80 | 0.80 | 0.80 |
| N-Hance ® 3198 | 0.0 | 0.20 | 0.50 | 1.50 | 0.0 |

TABLE 14-continued

| Ingredients | Example 43 | Example 44 | Example 45 | Example 46 | Example 47 |
|---|---|---|---|---|---|
| Cationic guar of Invention | 0.0 | 0.0 | 0.0 | 0.0 | 26.04 (5.76% active) |
| Methylparaben | 0.25 | 0.25 | 0.25 | 0.25 | 0.25 |
| Ammonyx ® 4002 | 0.10 | 0.10 | 0.10 | 0.10 | 0.10 |
| Bioterge ® AS-40 | 7.5 | 7.5 | 7.5 | 7.5 | 7.5 |
| Emerest ® 2400 | 1.00 | 1.00 | 1.00 | 1.00 | 1.00 |
| Crodasinic ® LS-30 | 6.66 | 6.66 | 6.66 | 6.66 | 6.66 |
| Amphosol ® CA | 6.66 | 6.66 | 6.66 | 6.66 | 6.66 |
| Propylene glycol | 0.50 | 0.50 | 0.50 | 0.50 | 0.50 |
| Glycerine | 0.50 | 0.50 | 0.50 | 0.50 | 0.50 |
| Disodium EDTA | 0.30 | 0.30 | 0.30 | 0.30 | 0.30 |
| Water | q.s to 100 | q.s to 100 | q.s to 100 | q.s to 100 | q.s to 100 |
| Total Liquid soap | 100 | 100 | 100 | 100 | 100 |
| Viscosity (cps) | 123 | 443 | 2130 | 23450 | 315 |
| PH | 8.66 | 8.57 | 8.28 | 8.72 | 8.3 |
| Lather drainage time (seconds) | 20.3 seconds | 30.3 seconds | | | 71.3 second |
| Polymer Mw | | 995,781 | 995,781 | 995,781 | 378,076 |
| Cationic DS | | 0.13 | 0.13 | 0.13 | 0.13 |

| (1) | Benecel ® MP943 | Hydroxypropyl-methylcellulose | Aqualon, Wilmington, DE |
| (2) | N-Hance ® 3198 | Guar hydroxypropyl trimmonium chloride | Aqualon, Wilmington, DE |
| (3) | Cat guar of invention (5.76% active) | Guar hydroxypropyl trimmonium chloride | Aqualon, Wilmington, DE |
| (4) | Methylparaben | Preservative | Clariant, Mt. Holly, NC |
| (5) | Ammonyx ® 4002 | Stearalkonium Chloride | Stepan Co. Northfield, IL |
| (6) | Bioterge ® As-40 | Na C14-C16 Olefin sulfonate (40%) | Stepan Co. Northfield, IL |
| (7) | Emerset ® 2400 | Glycol stearate | Cognis Inc. Amber, PA |
| (8) | Crodasinic ® LS-30 | Sodium Lauryl Sarcosinate | Croda Inc, Parsipanny, NJ |
| (9) | Propylene glycol, USP | | EM Industries, Gibbstown, NJ |
| (10) | Amphosol ® CA | Cocamidopropyl betaine (35% active) | Stepan Co. Northfield, IL |
| (11) | Disodium EDTA | | VWR |
| (12) | Glycerine Synthetic | | Spectrum Bulk Chemicals New Brunswick, NJ |

The polymer of invention used in Example 47, Table 14 was made by a procedure similar to the procedure used for experiment Z in Example 6, Table 5 with the substitution of N-Hance 3198 cationic guar for PRECURSOR 2.

Examples 48-50

Comparative Examples Demonstrating Stability of Skin Lotions containing the Polymer of the Invention vs. Commercial High MW Cationic Guar Skin Lotion Preparation Method:

Part A: In 8 ounce jar water was weighed and then placed in an 80° C. water-bath. Natrosol® was sifted while mixing. Next, N-Hance® 3215 or polymer of this invention was added followed by glycerine.

Part B: In a separate container Emerest® 2400 weighed and placed in the 80° C. water bath. Remaining ingredients of Part B were added in the order listed while mixing. Part A.

Part A was slowly added to Part B while mixing. Temperature was maintained at 80° C.

Part C: Part C was added to Part A/B. Mixing was continued while cooling to 40° C. Next Germaben® product was added and cooling was continued while mixing. Viscosity was measured after 24 hours at 12 rpm, 25° C. using Brookfield® LVT viscometer.

The polymer of this invention in Example 50, Table 15 was made as described in Experiment Y, in Example 6, Table 5.

TABLE 15

| Ingredients | Example 48 | Example 49 | Example 50 |
|---|---|---|---|
| Part A | | | |
| Deionized water | 78.25 | 77.25 | 69.20 |
| Natrosol ® 250MR | 0.50 | 0.50 | 0.50 |
| N-Hance ® 3215 | 0.0 | 1.0 | 0.0 |
| Cationic guar of Invention | 0.0 | 0.0 | 9.05 (11.05% active) |
| Glycerine | 2.0 | 2.0 | 2.0 |
| Part B | | | |
| Emerest ® 2400 | 2.75 | 2.75 | 2.75 |
| Industrene ® 5016K | 2.50 | 2.50 | 2.50 |
| Drakeol ® 7 | 2.00 | 2.00 | 2.00 |
| Lipolan ® 98 | 0.50 | 0.50 | 0.50 |
| Crodacol ® C-95 | 0.25 | 0.25 | 0.25 |
| Part C | | | |
| Deionized water | 10.00 | 10.00 | 10.00 |
| Triethanolamine | 0.50 | 0.50 | 0.50 |
| Part D | | | |
| Germaben ® II | 0.75 | 0.75 | 0.75 |
| Water | q.s to 100 | q.s to 100 | q.s to 100 |
| Total Skin lotion | 100 | 100 | 100 |
| Viscosity (cps) | 1550 | Phase separation | 2800 |
| PH | 7.5 | | 7.2 |
| Polymer Mw | | 1,087,074 | 42,030 |
| Cationic DS | | | |

| | | |
|---|---|---|
| (1) Natrosol ® 250MR | Hydroxyethyl-cellulose | Aqualon, Wilmington, DE |
| (2) N-Hance ® 3215 | Guar hydroxypropyl trimmonium chloride | Aqualon, Wilmington, DE |
| (3) Cat guar of invention (11.05% active) | Guar hydroxypropyl trimmonium chloride | Aqualon, Wilmington, DE |
| (4) Industrene ® 5016K | Stearic acid | Witco Co. Memphis TN |
| (5) Drakeol ® 7 | Mineral oil | Penreco, Karrn City, PA |
| (6) Emerset ® 2400 | Glycol stearate | Cognis Inc. Amber, PA |
| (7) Lipolan ® 98 | Laneth-10 acetate | Lipo Chemicals, Inc., Patterson, NJ |
| (8) Crodacol ® C-95 | Cetyl alcohol | Croda Inc, Parsipanny, NJ |
| (9) Triathanolamine | | J. T. Baker, Phillipsburg, NJ |
| (10) Glycerine Synthetic | | Spectrum Bulk Chemicals New Brunswick, NJ |
| (11) Germaben ® II | Preservative | ISP Wayne, NJ |

In formulating lotions and creams, stability of the final formulation is a critical target for the formulator. As demonstrated in Example 49, the skin lotion emulsion with commercially available N-Hance 3215 showed phase separation due to instability. The lotion emulsion without the polymer of this invention, Example 48, had only about 1,500 cps viscosity, and was runny. The lotion emulsion with polymer of this invention was not only stable but had viscosity of about 2,800 cps, having more body when dispensed.

Examples 51-53

Comparative Examples Demonstrating Improved Formulation Aesthetics with the Polymer of the Invention vs. High MW Cationic Guar Sunscreen Preparation Method:

Part A: Weighed Drakeol in an 8 oz jar. Next jar was placed in a bath set at 70° C. The remaining ingredients of Part A were added in the order listed, while mixing. Mixing was continued for 30 minutes at 70° C.

Part B: In a separate jar water was weighed and then placed in 70° C. water-bath. Natrosol® polymer was added to water while mixing. Next remaining ingredients of Part B were added while mixing at 70° C.

Part C: Premixed Part C. Part C was added to Part B once all ingredients in Part B were dissolved. Part B/C was then added to Part A once it had reached to 70° C. while mixing. Mixing was continued for 30 minutes at 70° C.

Part D: The above Part A/B/C mixture was removed from the water bath and was allowed to cool to 50° C. while mixing. Germaben II product was added once temperature reached 50° C. Mixing was continued until the sunscreen emulsion reached room temperature.

The polymer of the Invention in Example 53, Table 16, was prepared by process described in experiment U, Example 6, Table 5, substituting N-Hance 3198 polymer for N-Hance 3215.

TABLE 16

| Ingredients | Example 51 | Example 52 | Example 53 |
|---|---|---|---|
| Part A | | | |
| Drakeol ® 7 | 13.00 | 13.00 | 13.00 |
| Arlamol ® E | 6.00 | 6.00 | 6.00 |
| Neo Heliopan ® AV | 3.00 | 3.00 | 3.00 |
| Uvinol ® M40 | 0.0 | 0.0 | 9.05 |
| Castor ® Wax | 1.40 | 1.40 | 1.40 |
| Crill-6 | 1.20 | 1.20 | 1.20 |
| Arlatone ® T | 1.00 | 1.00 | 1.00 |
| Ozokerite ® | 1.00 | 1.00 | 1.00 |
| Dehymuls ® HRE7 | 0.50 | 0.50 | 0.50 |
| Part B | | | |
| Deionized Water | 40.50 | 39.50 | 30.72 |
| Natrosol ® 250HHR CS | 0.50 | 0.50 | 0.50 |
| N-Hance ® 3198 | 0.00 | 1.00 | 0.00 |
| Product of this invention | 0.00 | 0.00 | 9.78 |
| Glycerine | 3.00 | 3.00 | 3.00 |
| Part C | | | |
| Deionized Water | 23.10 | 23.10 | 23.10 |
| Magnesium sulfate | 0.70 | 0.70 | 0.70 |
| Part D | | | |
| Germaben II | 0.1 | 0.1 | 0.1 |
| Sunscreen | | | |
| Viscosity (cps) | 4310 | 13250 | 5570 |
| PH | 6.3 | 5.9 | 6.0 |
| Polymer Mw | | 1,079,887 | 60,711 |
| Cationic DS | | | |

| | | |
|---|---|---|
| (1) Natrosol ® 250 HHR CS | Hydroxyethyl-cellulose | Aqualon, Wilmington, DE |
| (2) N-Hance ® 3198 | Guar hydroxypropyl trimmonium chloride | Aqualon, Wilmington, DE |
| (3) Cat guar of invention (10.23% active) | Guar hydroxypropyl trimmonium chloride | Aqualon, Wilmington, DE |
| (4) Arlamol ® E | PPG-15 Stearyl ether | Uniqema Americas New Castle, DE |
| (5) Drakeol ® 7 | Mineral oil | Penereco, Karrn City, PA |
| (6) Neo Heliopan ® HV | Octyl methoxycinnamate | Symrise, Totowa, NJ |
| (7) Uvinol ® M40 | Benzophenone-3 | BASF, Mount Olive, NJ |
| (8) Castor Wax | Hydrogenated castor oil | Frank B Ross |
| (9) Arlatone ® T | PPG-40 Sorbitan peroleate | Uniqema Americas New Castle, DE |
| (10) Ozokerite ® Wax | wax | Frank B. Ross |
| (11) Dehymuls ® HRE7 | PEG-7 hydrogenated Castor oil | Cognis, Amber, PA |
| (12) Germaben ® II | Preservative | ISP Wayne, NJ |
| (13) Glycerine Synthetic | | Spectrum Bulk Chemicals New Brunswick, NJ |
| (14) Magnesium sulfate | | J.T. Baker, Phillpsburg, NJ |

Creamy, glossy, emulsions are desirable when formulating sun care lotions. It is also desirable to generate enough viscosity to prevent the lotion from dripping or having a runny consistency, but not be too thick and difficult to spread. The sunscreen (Example 52) made with commercial cationic guar N-Hance® 3198 was slightly grainy and had off-white color in addition to being very high in viscosity. The sunscreen made with product of this invention (Example 52) was not only comparable in viscosity to the sunscreen without the conditioning polymer (Example 51) but was also glossy, white and stable as Example 51.

Examples 54-62

Comparative Examples Demonstrating Improved Stability and Consistency for Laundry Detergents and Fabric Softeners Containing the Polymer of Invention vs. High MW Cationic Guar In formulating liquid laundry detergents and fabric softeners, the stability of the formulation and its consistency are important to delivering the performance of the product. A high viscosity formulation may not mix readily in the washer, leading to poor cleansing or fabric conditioning. Poor stability in a formulation, and gross phase separation of the ingredients also negatively impacts performance.

The polymer of this invention described in Table 17 was prepared according to the process described for experiment Y in Example 6, Table 5.

As shown in Table 17, the polymer of this invention was post-added at 0.2% active level to commercially available Tide® liquid laundry detergent from Procter & Gamble Co. of Cincinnati, Ohio and to Wisk liquid laundry detergent from Unilever, Greenwich Conn. 0.2% of commercially available N-Hance® 3215 cationic guar was post-added to these laundry detergents.

TABLE 17

| | Example | | |
|---|---|---|---|
| | 54 | 55 | 56 |
| Laundry detergent | Tide ® as received | Tide ® with 0.2% of product of invention | Tide ® with 0.2% N-Hance ® 3215 |
| Viscosity at 12 rpm | 202 cps | 214 cps | 341 cps |
| PH | 8.0 | 7.9 | 7.8 |
| Comments % T at 600 nm | Clear blue | Slightly hazy blue | Hazy with settling |

| | Example | | |
|---|---|---|---|
| | 57 | 58 | 59 |
| Laundry Detergent | Wisk ® as received | Wisk ® with 0.2% of product of invention | Wisk ® with 0.2% N-Hance ® 3215 |
| Viscosity at 12 rpm | 100 cps | 95 cps | 260 cps |
| PH | 7.5 | 7.4 | 7.4 |
| Comments % T at 600 nm | Hazy blue | Hazy blue | Opaque with settling |

TABLE 17-continued

| | Example | | |
|---|---|---|---|
| | 60 | 61 | 62 |
| Fabric softener | Downy ® as received | Downy ® with 0.2% of product of invention | Downy ® with 0.2% N-Hance ® 3215 |
| Viscosity at 12 rpm | 120 cps | 150 cps | Gel-like |
| PH | 3.2 | 3.5 | 3.6 |
| Comments % T at 600 nm | Opaque | Opaque | Opaque |

The product of this invention had no effect on the viscosity of the original liquid laundry detergent and, it was also compatible (Examples 55 and 58). The N-Hance® 3215 product was found to be not compatible (Examples 56 and 59).

In a Fabric softener the polymer of the invention had no significant impact on the viscosity, and it was stable to pH 3 to 3.5 (Example 61). In contrast, the commercially available N-Hance® 3215 polymer caused the commercial fabric softener to gel (Example 62), making it unusable.

Examples 63-69

Comparative Examples Demonstrating the Improved Effect of Polymer of Invention on Conditioning Body Wash Viscosity vs. High MW Cationic Guar: For Polymers Prepared by Peroxide Degradation Process and Combined Biochemical-Peroxide Processing Body washes made with the polymer of the invention in Examples 65 and 66, Table 18, had lower viscosity as compared with commercially available N-Hance® 3000 product, Example 64. In Example 65, the polymer was made with peroxide degradation according to the procedure described for experiment AC in Example 6, Table 5. In Example 66, the polymer was made by sequential treatment with peroxide followed by enzyme degradation, as described in Example 8C.

Body washes in Table 19 made with the polymer of the invention (Examples 68-69) had much lower viscosity compared to the body wash made with PRECURSOR 3 (Example 67). In fact, the wash made with PRECURSOR 3 was almost like a gel. The polymer of the invention used in Example 68 was made with peroxide degradation, as described in experiments AA and AB in Example 6, Table 5. The polymer of invention used in Example 69, was made by sequential treatment with enzyme followed by peroxide degradation, as described in Example 8B.

TABLE 18

| Ingredients | Example 63 | Example 64 | Example 65 | Example 66 |
|---|---|---|---|---|
| Deionized water | 118.75 | 114.68 | 43.75 | 43.75 |
| Rhodapex ES-STD | 87.5 | 87.5 | 87.5 | 87.5 |
| N-Hance ® 3000 | 0.0 | 4.072 | 0.0 | 0.0 |
| Cationic guar of Invention (5% active) | 0.0 | 0.0 | 75.0 | 75.0 |
| Amphosol ® CA | 30.0 | 30.0 | 30.0 | 30.0 |
| Ninol ® COMF | 5.0 | 5.0 | 5.0 | 5.0 |
| Sodium Chloride 20% | 6.0 | 6.0 | 6.0 | 6.0 |

TABLE 18-continued

| Ingredients | Example 63 | Example 64 | Example 65 | Example 66 |
|---|---|---|---|---|
| Glydant ® | 1.25 | 1.25 | 1.25 | 1.25 |
| Citric Acid (5%) | Adjust pH | Adjust pH | Adjust pH | Adjust pH |
| Water | q.s to 250 | q.s to 250 | q.s to 250 | q.s to 250 |
| Total Shower gel | 250 | 250 | 250 | 250 |
| Viscosity (cps) | 9550 | 75000 | 27100 | 22230 |
| PH Polymer | 5.3 | 5.15 | 5.25 | 5.31 |
| Mw | | 923655 | 330717 | 131308 |
| Cationic DS | | 0.06 | 0.06 | 0.06 |

All viscosities were measured at 12 rpm, 2 min of spindle rotation using Brookfield LVT. Samples were conditioned at 25° C.

| (2) | N-Hance ® 3000 | Guar hydroxypropyl trimmonium chloride | Aqualon, Wilmington, DE |
|---|---|---|---|
| (3) | Cat guar of invention (5.0% active) | Guar hydroxypropyl trimmonium chloride in Example 65 | Aqualon, Wilmington, DE |
| (3) | Cat guar of invention (5.0% active) | Guar hydroxypropyl trimmonium chloride in Example 66 | Aqualon, Wilmington, DE |
| (4) | Rhodapex ® ES-STD | Sodium Laureth (3) sulfate | Rhodia, Cranberry, NJ |
| (5) | Amphosol ® CA | Cocamidopropyl betaine | Stepan Co., Northfield, Il |
| (6) | Ninol COMF | Cocamide MEA | Stepan Co., Northfield, Il |
| (7) | Glydant ® | DMDMHydantion | Lonza Corp, Fair Lawn, NJ |
| (8) | Citric Acid | | J. T. Baker, Philipsburg, NJ |

TABLE 19

| Ingredients | Example 67 | Example 68 | Example 69 |
|---|---|---|---|
| Deionized water | 114.52 | 43.75 | 43.75 |
| Rhodapex ES-STD | 87.5 | 87.5 | 87.5 |
| N-Hance ® 3000 | 4.235 | 0.0 | 0.0 |
| Cationic guar of Invention (5% active) | 0.0 | 75.0 | 75.0 |
| Amphosol ® CA | 30.0 | 30.0 | 30.0 |
| Ninol ® COMF | 5.0 | 5.0 | 5.0 |
| Sodium Chloride 20% | 6.0 | 6.0 | 6.0 |
| Glydant ® | 1.25 | 1.25 | 1.25 |
| Citric Acid (5%) | Adjust pH | Adjust pH | Adjust pH |
| Water | q.s to 250 | q.s to 250 | q.s to 250 |
| Total Shower gel | 250 | 250 | 250 |
| Viscosity (cps) | Gel-like | 65200 | 35750 |
| pH Polymer | 5.4 | 5.3 | 5.4 |
| Mw | 999145 | 719515 | 963759 |
| Cationic DS | 0.9 | 0.9 | 0.9 |

All viscosities were measured at 12 rpm, 2 min of spindle rotation using Brookfield LVT. Samples were conditioned at 25° C.

| (2) | PRECURSOR 3 | Gar hydroxypropyl trimmonium chloride | Aqualon, Wilmington, DE |
|---|---|---|---|
| (3) | Cat guar of invention (5.0% active) | Guar hydroxypropyl trimmonium chloride in Example 68 | Aqualon, Wilmington, DE |
| (3) | Cat guar of invention (5.0% active) | Guar hydroxypropyl trimmonium chloride in Example 69 | Aqualon, Wilmington, DE |
| (4) | Rhodapex ® ES-STD | Sodium Laureth (3) sulfate | Rhodia Cranberry, NJ |
| (5) | Amphosol ® CA | Cocamidopropyl betaine | Stepan Co. Northfield, Il |
| (6) | Ninol COMF | Cocamide MEA | Stepan Co. Northfield, Il |
| (7) | Glydant ® | DMDMHydantion | Lonza Corp, Fair Lawn, NJ |
| (8) | Citric Acid | | J. T. Baker, Philipsburg, NJ |

Table 20: Oxidative Group Content of Polymers of the Invention

The results in Table 20 show the differences in composition between materials of the invention prepared by procedures in Examples 6, 7, or 8a, b, c versus Example 8d and versus the commercial high molecular weight cationic commercial polymers in the marketplace. Solutions of the polymers were analyzed using a method specific for detection of aldehyde groups (Analytical Biochemistry, 1983, 134, 499-504). The results from these tests are shown by the colorimetric test results in Table 20 as absorbance at 595 nm/gram polymer, or as milliequivalent aldehyde/gram polymer.

As shown by the results in Table 20, materials of the invention prepared by procedures in Examples 6, 7, or 8a-c produced materials having significant absorbance, as measured by the Purpald method [H. B. Hopps, Aldrichimica ACTA, 2000, 33(1), 28-30] This method is specific for detection of aldehydes. Negligible absorbance was detected in materials by this method, that were prepared according to the procedure in Example 8d or in the starting cationic guar or other commercial cationic guar materials.

These results indicate that materials prepared through treatments that include an oxidative agent, as a single reactive treatment, or in combination with hydrolytic enzyme treatment, will produce a low molecular weight material with a measurable amount of aldehyde groups on the polymer. Using an indirect iodometric titration, the level of aldehyde in some samples was quantified and a calibration equation was created to convert from Absorbance/gram to milliequivalent aldehyde/gram. As determined by this method, the level of aldehyde groups in the materials of the invention is at least 0.001 meq/g. The calibration equation is shown in equation 2. The meq/gram aldehyde values shown in Table 20 were determined from equation (2), with the exception of Example 8-4, which was measured directly. For example 9 in Tables 20 and 21, the aldehyde content was determined by sugar analysis of the acid-hydrolyzed guar product using HPLC, to obtain the ratio of galactose/mannose for the starting cationic guar precursor and the oxidized cationic guar product. The aldehyde content of the oxidized cationic guar was 23%, corresponding to 0.41 mmole aldehyde/gram polymer.

$$\text{absorbance/gram} = 445.52(\text{meq aldehyde/g}) + 0.9953 \quad (2)$$

TABLE 20

Aldehyde and Weight Average Molecular Weight of Cationic Oxidized Polygalactomannans

| Example | Experiment Example | Average MW | Absorbance/gram polymer[1] | Aldehyde meq/gram |
|---|---|---|---|---|
| Example 6. Chemical Decomposition Process with Oxidative Reagent | | | | |
| 6-1 | U | 417,000 | 4.78 | 0.0085 |
| 6-2 | U | 119,000 | 5.65 | 0.01035 |
| 6-3 | W | 919,000 | 1.84 | 0.0019 |
| 6-4 | W | 434,000 | 4.12 | 0.007 |
| 6-5 | W | 292,000 | 3.85 | 0.00625 |
| 6-6[2] | W | | 4.20 | 0.0072 |
| Example 8a-c. Biochemical Decomposition Process Couples with Oxidative Reagent | | | | |
| 8a-1 | | 63,000 | 5.88 | 0.0109 |
| 8a-2 | | 52,800 | 8.6 | 0.0600 |
| 8a-3 | | 36,100 | 13.64 | 0.02835 |
| 8a-4 | | 38,800 | 13.01 | 0.0269 |
| Example 8d. Biochemical Process with No Oxidative Reagent | | | | |
| 8d-1 | | 55,000 | 0.16 | 0 |
| 8d-2 | | 44,700 | 0.28 | 0 |
| Example 9. Biochemical Process with Biochemical Oxidation Reagent | | | | |
| 9 | | 40,000 | | 0.41 |
| Commercial Cationic Polymers | | | | |
| N-Hance 3215 | | 1,200,000 | 1.4[3] | 0 |
| N-Hance 3196 | | 1,400,000 | 0.55 | 0 |
| Jaguar C162 | | 1,070,000 | 0 | 0 |
| Jaguar Excel | | 1,200,000 | 0 | 0 |
| Ucare Polymer JR400 | | 500,000 | 0.78 | 0 |
| Reagent Blank | | | 0.09 | 0 |

[1]Aldrichimica ACTA, 2000, V33, No 1., p 28-30
[2]Ammonium Persulfate Used in Place of Hydrogen Peroxide in Process
[3]Turbidity and haze in sample gave value of 1.4-no purple color detected

TABLE 21

Product of This Invention

| Table | Example | Experiment | Precursor | Viscosity, cP #4 at 0.3 rpm | Viscosity, cP #4 at 30 rpm | % Polymer Solids | Molecular weight | Aldehyde meq/g of polymer |
|---|---|---|---|---|---|---|---|---|
| 1A | 1 | A | N-Hance 3205 | 12,000 | 60 | 10 | 2,803 | |
| 1A | 1 | B | N-Hance 3205 | 6,000 | 120 | 10 | 16,653 | |
| 1A | 1 | C | N-Hance 3205 | 10,000 | 240 | 10 | 3,597 | |
| 1A | 1 | D | N-Hance 3205 | 4,000 | 160 | 10 | 21,608 | |
| 1A | 1 | E | N-Hance 3205 | 6,000 | 480 | 10 | 39,733 | |
| 1A | 1 | F | N-Hance 3205 | Not available | Not available | 10 | 91,000 | |
| 2 | 2 | G | N-Hance 3205 | 30,000 | 1,980 | 10 | 160,050 | |
| 2 | 2 | H | N-Hance 3205 | 84,000 | 1,180 | 10 | 273,128 | |
| 2 | 2 | I | N-Hance 3205 | 1,014,000 | >20,000 | 10 | 610,515 | |
| 2 | 3 | J | N-Hance 3215* | 12,000 | 580 | 10 | 57,758 | |
| 5 | 6 | S | N-Hance 3215* | 12,000 | 580 | 10 | 57,768 | |
| 2 | 3 | K | N-Hance 3215* | 18,000 | 1,300 | 10 | 109,318 | |
| 5 | 6 | T | N-Hance 3215* | 18,000 | 1,300 | 10 | 109,318 | |
| 2 | 3 | L | N-Hance 3215* | 110,000 | >20,000 | 10 | 353,145 | |
| 3 | 4 | M | JAGUAR C13S | 74,000 | >20,000 | 10 | 317,145 | |
| 3 | 4 | N | JAGUAR C-162 | 50,000 | >20,000 | 10 | 555,532 | |
| 3 | 4 | O | N-Hance 3215* | 6,000 | 180 | 10 | 52404 | |
| 4 | 5 | P | 3205 | 40,000 | 2,500 | 10 | 141,033 | |
| 4 | 5 | Q | 3205 | 148,000 | 11,920 | 10 | 238,607 | |
| 4 | 5 | R | 3205 | 956,000 | >20,000 | 10 | 622,745 | |
| | 6 Method U | U** | N-Hance 3198* | 12,000 | 800 | 10 | 50,400 | |
| | 6 Method U | U** | N-Hance 3198* | 18,000 | 660 | 10 | 42,700 | |
| | 6 Method U | U** | N-Hance 3215* | 16,000 | 1,120 | 10 | 70,700 | |
| | 6 | Z** | PRECURSOR 2 * | 6,000 | 240 | 5 | 367,000 | |
| | 6 | Z** | N-Hance 3198* | 16,000 | 3,320 | 5 | 407000 | |
| | 6 | Z** | 3205 | 52,000 | 11,180 | 5 | 548000 | |
| | 6 | Z** | PRECURSOR 4 * | 8,000 | 100 | 5 | 247000 | |
| | 6 | Z** | PRECURSOR 4 * | 6,000 | 760 | 5 | 686000 | |
| | 6 | Z** | PRECURSOR 2* | 2,000 | 80 | 5 | 27,900 | |
| | 6 Method U | U** | N-Hance 3215* | 8,000 | 440 | 10.00 | 50,200 | |
| | 6 Method U | U** | N-Hance 3215* | 76,000 | 6,000 | 10.00 | 197,000 | |
| | 6 Method U | U** | Cat.HEC | 4,000 | 360 | 10 | 179,000 | |
| 5 | 6 Method AC | AC | N-Hance 3000* | 24,000 | 2,780 | 5 | 334,000 | |
| | 6 Method AC | AC** | N-Hance 3000* | 6,000 | | 5 | 329,000 | |
| | 8C | | N-Hance 3000* | 10,000 | 140 | 5 | 131,000 | |
| 5 | 6 | AA | Precursor 3 | 10,000 | 1,080 | 5 | 719,000 | |
| 5 | 6 | AB | Precursor 3 | 8,000 | 40 | 5 | 191,000 | |
| | 8b | | Precursor 3 | 24,000 | 4,180 | 5 | 964,000 | |
| | 8b | | Precursor 3 | 10,000 | 320 | 5 | 711,551 | |

TABLE 21-continued

Table 21

| | | | | Product of This Invention | | | | |
|---|---|---|---|---|---|---|---|---|
| Table | Example | Experiment | Precursor | Viscosity, cP #4 at 0.3 rpm | Viscosity, cP #4 at 30 rpm | % Polymer Solids | Molecular weight | Aldehyde meq/g of polymer |
| | 8b | | Precursor 3 | 4,000 | 160 | 5 | 577,412 | |
| | 8b | | Precursor 3 | 10,000 | 200 | 5 | 651239 | |
| | 8b | 8b2 | Precursor 3 | 2,000 | 40 | 5 | 292,933 | 0.00588 |
| | 6 Method AA | AA** | 3000* | 16,000 | 5,740 | 5 | 298,219 | 0.00882 |
| 5 | 6 | Y | 3215* | 10,000 | 640 | 11 | 42,030 | 0.00267 |
| 9 | | | 3215 | | 120 | | 40,000 | 0.41 |
| | 70 | | 50/50 N-Hance 3000*/Polymer LR30M | 8,000 | 720 | 10 | 97374 | 0.00267 |
| | 72-1 | AC plus chitosan*** | 80/20 N-Hance 3000 plus Chitosan | 14000 | 2220 | 5 | 334000 | |
| | 72-2 | 8B plus Chitosan*** | 90/10 PRECURSOR 3 plus Chitosan | 8000 | 3920 | 5 | 964000 | |

*The polymer was preblended with 2 to 3% Fumaric Acid
**Peroxide and precursor polymer was varied to obtain polymer of invention listed in experiment
Viscosities were measured using Brookfield LVT viscometer Model DV-I+
At 30 rpm maximum viscosity reading possible is 20,000 cps
At 0.3 rpm maximum viscosity reading possible is 2,000,000 cps
***Chitosan from Vanson Incorporated has 88% deacetylation and 1.0% Brookfield viscosity of 660 cps Test strips coated with the Purpald reagent (E-M Science) were also used to measure aldehyde content in samples prepared by the methods in Examples 6 and 8a-c. These results are shown in Table 21 along with the viscosity data and MW data for the products of this invention. Combined together, the results in Tables 20 and 21 demonstrate that the products of this invention have an aldehyde content of at least 0.001 meq/gram and the lower Brookfield viscosity limit for the products of this invention is 40 cps at 30 rpm, 25 C, sp. 4 and the upper Brookfield viscosity limit is 2,000,000 cps at 0.3 rpm, 25 C, sp.4.

Example 70

Chemical Oxidative Process for Polymer Blend

Preparation of low molecular weight liquid cationic polysaccharide from high molecular weight cationic polysaccharide Blend:

50 g of 0.06 cationic DS was blended with 50 g of Cationic HEC (Polymer LR30M from Dow Chemical, Midland Mich.) and with 1.25 g of fumaric acid. 816 g of water was heated to about 90° C. Next 75 g of 1.0% hydrogen peroxide was added. Mixed for about 30 minutes and then 18.1 g of 1.0% hydrogen peroxide was added. Two additional additions of 18.1 g of 1.0% hydrogen peroxide were made at about 30 minutes interval while mixing. Mixed for about 90 minutes after the last peroxide addition. Next 0.95 grams of sodium meta bisulfite was added. The solution was preserved with 0.5% Phenoxetol and 0.18% Nipasept sodium. Detail on the polymer of invention of this experiment is provided in Table 21.

This example demonstrates that the polymers of the present invention can be prepared using blends of functional polymers.

Example 71

The following examples demonstrate that the low molecular weight cationic oxidized polysaccharides of this invention can be incorporated into personal care formulations containing silicone materials, and the viscosities of the resulting products are significantly reduced when compared to the viscosities of silicone formulations containing high molecular weight commercial cationic polysaccharides available in the marketplace. The silicone materials can be in the form of polymers or oligomers of a cyclosiloxane, linear siloxane, hydroxy terminated siloxane, comb or graft siloxane structure with polyol, amino, or other functional groups present in the siloxane structure.

An anionic shampoo formulation was used for these Experiments comprised of the ingredients in Table 22. The formulation was prepared by mixing the surfactants and water at 60 C for 1 hour, cooling the mixture to 35 C and adding the silicone emulsion. The shampoos contained GE Silicones emulsion SM555 at 0.5 wt % silicone content. The low molecular weight cationic guar from Example 6, Table 5, experiment Y was incorporated into the shampoo in Example 71-1 and compared with shampoos containing high MW commercial cationic guars in Examples 71-2 through 71-5 and with a commercial shampoo in Example 71-6. Viscosities of the shampoos were measured using a Brookfield LVT viscometer, sp. 4, at 0.3 and 30 rpm at room temperature.

TABLE 22

| | | | | Shampoo | | |
|---|---|---|---|---|---|---|
| Example 71 Formulation Ingredient | Tradename | Manufacturer | pH | viscosity/cps 0.3 rpm | viscosity/cps 30 rpm | 30 days @ 25 C. |
| Ammonium Lauryl Sulfate | Stepanol AM | Stepan Company, Northfield, Illinois | | | | |
| Ammonium Lauryl Ether Sulfate | Steol CA-330 | Stepan Company, Northfield, Illinois | | | | |

TABLE 22-continued

Example 71

| Formulation Ingredient | Tradename | Manufacturer | pH | Shampoo viscosity/cps 0.3 rpm | viscosity/cps 30 rpm | 30 days @ 25 C. |
|---|---|---|---|---|---|---|
| Cocamidopropyl betaine | Amphosol CA | Stepan Company, Northfield, Illinois | | | | |
| Deionized Water | | | | | | |
| Dimethicanol Emulsion | SM555 | GE Silicones, Waterford, NY | | | | |
| Guar hydroxypropyltrimonium chloride | | | 6 | 42,000 | 14,100 | Stable |
| Hydroxypropylguar hydroxypropyltrimonium chloride | | | 6.2 | 102,000 | 36,600 | Stable |
| Guar hydroxypropyltrimonium chloride | | | 6.1 | 136,000 | 44,050 | Stable |
| Guar hydroxypropyltrimonium chloride | | | 6 | 132,000 | 36,300 | Stable |
| Guar hydroxypropyltrimonium chloride | | | 6.1 | 198,000 | 43,200 | Stable |
| Commercial Product Silicone Shampoo with guarhydroxypropyltrimonium chloride | | Helene Curtis | | | 10,200 | Stable |

The results in Table 22 demonstrate that desirable shampoo viscosities are obtained with the polymer of the invention and the shampoos show no phase separation. The shampoos formulated with the commercial cationic polymers of high MW are undesirably viscous and difficult to pour. Blends of the cationic oxidized polysaccharides of this invention with other water soluble polymers can also be incorporated into personal care formulations containing silicone polymers and oligomers to produce stable systems.

The cationic oxidized polysaccharides of this invention and its binary and tertiary blends with other functional polymers, e.g., chitosan, polyvinylpyrrolidone homopolymers and copolymers, acrylamide homopolymers and copolymers, high MW cationic hydroxyethylcellulose, high Mw cationic guars, and hydrophobic polymers (also known as associative polymers) can be designed to improve the formulation aesthetics (i.e., foaming), stability, delivery and deposition efficiency of conditioning oils such as silicones or other conditioning agents to hair, skin, and textile substrates. These blends may also improve delivery efficiency of other ingredients, such as antimicrobial compounds, antidandruff compounds, conditioning agents, fragrances, sunscreen actives, emmolients, moisturizers, medicaments such as anti-psoriasis medicines, styling aids such as polyvinylpyrrolidone copolymers, sizing agents, etc. to hair, skin, and textile substrates. Some blends of the polymer of this invention with water soluble functional polymers are demonstrated in Example 72, and the viscosities of the blends are shown in Table 21. A variety of polymer blends with the polymers of this invention can be prepared, and this example is not intended to be all-inclusive.

Example 72

This example demonstrates that the polymers of the present invention can be blended with other functional polymers. The viscosity of each blend is shown in Table 21.

A 5% dispersion of chitosan (Vanson Incorporated, Redmond, Wash.; 88% deacetylation, 1% viscosity: 660 cps) was prepared by mixing 2.1 grams chitosan with a 6% dispersion of fumaric acid. Two blends were prepared using this dispersion:

72-1 25.3 grams of the chitosan dispersion was mixed with 90.5 grams of Ex. 6 Experiment AC to produce a dispersion. The 24 hour viscosity of this dispersion was measured on a Brookfield viscometer at 0.3 and 30 rpm at ambient temperature and found to be 14,000 and 2,220 cps, respectively.

72-2 11.4 grams of the chitosan dispersion was mixed with 94.1 grams of Ex. 8B (MW 964,000) to produce a dispersion. The 24 hour viscosity of this dispersion was measured on a Brookfield viscometer at 0.3 and 30 rpm at ambient temperature and found to be 8,000 and 3,920 cps, respectively.

While the invention has been described with respect to specific embodiments, it should be understood that the invention should not be limited thereto and that many variations and modifications are possible without departing from the spirit and scope of the invention.

What is claimed:

1. Personal care or household care composition comprising at least one cationic, oxidized polysaccharide or derivative thereof having a weight average molecular weight with a lower limit of 42030 and an upper limit of 1,000,000, having aldehyde functionality content of at least 0.001 meq/gram of polysaccharide, wherein the personal care or household care composition containing 1.82% by weight of the cationic, oxidized polysaccharide or derivative thereof has a light transmittance of 83.8% at a wavelength of 600 nm in an aqueous solution.

2. The personal care or household care compositions of claim 1, wherein the at least one cationic, oxidized polysaccharide or derivative thereof has a Brookfield viscosity at 10 wt % solids of the polysaccharide at 25° C. of a lower limit of 30 cps and an upper limit of 2,000,000 cps.

3. The composition of claim 1 wherein the composition has a cationic degree of substitution (DS) lower limit of about 0.001 and an upper limit of about 3.0.

4. The composition of claim 3, wherein the cationic degree of substitution (DS) has a lower limit amount of 0.01.

5. The composition of claim 3, wherein the cationic degree of substitution (DS) has a lower limit amount of 0.05.

6. The composition of claim 3, wherein the cationic degree of substitution (DS) has a lower limit amount of 0.1.

7. The composition of claim 3, wherein to cationic degree of substitution (DS) has an upper limit of about 2.0.

8. The composition of claim 3, wherein the cationic degree of substitution (DS) has an upper limit of about 1.0.

9. The composition of claim 3, wherein the cationic degree of substitution (DS) has an upper limit of about 0.5.

10. The composition of claim 3, wherein the cationic degree of substitution (DS) has an upper limit of about 0.25.

11. The composition of claim 1, wherein the derivative moiety onto cationic derivatized polysaccharide is selected from the group consisting of alkyl, hydroxyalkyl, alkylhydroxyalkyl, and carboxymethyl, wherein the alkyl has a carbon chain containing from 1 to 22 carbons and the hydroxyalkyl is selected from the group consisting of hydroxyethyl, hydroxypropyl, and hydroxybutyl.

12. The composition of claim 1, wherein to polysaccharide is selected from the group consisting of cellulose, starch, dextran, and polygalactomannan.

13. The composition of claim 12, wherein to polysaccharide is a polygalactomannan that is either guar or locust bean or derivatives thereof.

14. The composition of claim 12, wherein the polysaccharide is a cellulosic that is a cellulose ether derivative.

15. The composition of claim 1, wherein to cationic moiety is selected from quaternary ammonium compounds.

16. The composition of claim 15, wherein the quaternary ammonium compound is selected from the group consisting of 3-chloro-2-hydroxypropyltrimethylammonium chloride, 2,3-epoxy-propyltrimethylammonium chloride, 3-chloro-2-hydroxypropyltrimethylammonium bromide, 2,3-epoxy-propyltrimethylammonium bromide; glycidyltrimethylammonium chloride, glycidyltriethylammonium chloride, gylcidyltripropylammonium chloride, glycidylethyldimethylammonium chloride, glycidyldiethylmethylammonium chloride, and their corresponding bromides and iodides; 3-chloro-2-hydroxypropyltrimethylammonium chloride, 3-chloro-2-hydroxypropyltriethylammonium chloride, 3-chloro-2-hydroxypropyltripropylammonium chloride, 3-chloro-2-hydroxypropylethyldimethylammonium chloride, and their corresponding bromides and iodides; and halides of imidazoline ring containing compounds.

17. The composition of claim 1, wherein the Mw has a lower limit of 50,000.

18. The composition of claim 1, wherein the Mw has a lower limit of 75,000.

19. The composition of claim 1, wherein the Mw has a lower limit of 100,000.

20. The composition of claim 1, wherein the Mw has an upper limit of 600,000.

21. The composition of claim 1, wherein the Mw has an upper limit of 300,000.

22. The composition of claim 1, wherein the Mw has an upper limit of 150,000.

23. The composition of claim 2, wherein the lower limit of the Brookfield viscosity at 30 rpm of the polysaccharide is 50 cps.

24. The composition of claim 2, wherein the lower limit of the Brookfield viscosity at 30 rpm of the polysaccharide is 100 cps.

25. The composition of claim 2, wherein the lower limit of the Brookfield viscosity at 30 rpm of the polysaccharide is 300 cps.

26. The composition of claim 2, wherein the upper limit of the Brookfield viscosity at 30 rpm of the polysaccharide is 10,000 cps.

27. The composition of claim 2, wherein the upper limit of the Brookfield viscosity at 30 rpm of the polysaccharide is 5,000 cps.

28. The composition of claim 2, wherein the upper limit of the Brookfield viscosity at 30 rpm of the polysaccharide is 2,000 cps.

29. The composition of claim 2, wherein the lower limit of the Brookfield viscosity at 0.3 rpm of the polysaccharide is 50,000 cps.

30. The composition of claim 2, wherein the lower limit of the Brookfield viscosity at 0.3 rpm of the polysaccharide is 100,000 cps.

31. The composition of claim 2, wherein the lower limit of the Brookfield viscosity at 0.3 rpm of the polysaccharide is 150,000 cps.

32. The composition of claim 2, wherein the upper limit of the Brookfield viscosity at 0.3 rpm of the polysaccharide is 1,000,000 cps.

33. The composition of claim 2, wherein the upper limit of the Brookfield viscosity at 0.3 rpm of the polysaccharide is 500,000 cps.

34. The composition of claim 2, wherein the upper limit of the Brookfield viscosity at 0.3 rpm of the polysaccharide is 250,000 cps.

35. The composition of claim 1, further comprising a member selected from the group consisting of colorant, preservative, antioxidant, alpha or beta hydroxy acid, activity enhancer, emulsifier, functional polymer, viscosifying agent alcohol, fat or fatty compound, antimicrobial compound, anti-dandruff, volumizers, anti-static agents, moisturizers, styling-aids, zinc pyrithione, silicone material, hydrocarbon polymer, emollients, oil, surfactants, suspending agents, suncare agent and mixtures thereof.

36. The composition of claim 35, wherein the member is a functional polymer that is selected from the group consisting of anionic, hydrophobically-modified, and amphoteric acrylic acid copolymers, vinylpyrrolidone homopolymers and copolymers, cationic vinylpyrrolidone copolymers, nonionic, cationic, anionic, and amphoteric cellulosic polymers, acrylamide homopolymers, cationic, anionic, amphoteric, and hydrophobically-modified acrylamide copolymer, polyethylene glycol polymer and copolymer, hydrophobically-modified polyether, hydrophobically-modified polyetheracetal, hydrophobically-modified polyetherurethane, an associative polymer, hydrophobically-modified cellulosic polymer, polyethyleneoxido-propylene oxide copolymer, chitosan, clay, and a nonionic, anionic, hydrophobically-modified, amphoteric, cationic polysaccharides, chitosan, starch, alginates, Konjack gum, clay, poloxamer (polyoxyethylene/polyoxypropylene block polymer), and mixtures thereof.

37. The composition of claim 35, wherein, the member is the nonionic, cationic, anionic, and amphoteric cellulosic polymers are selected from the group consisting of hydroxyethylcellulose, hydroxypropylcellulose, hydroxypropylmethylcellulose, carboxymethylcellulose, hydrophobically-modified carboxymethylcellulose, cationic hydroxyethylcellulose, cationic hydrophobically-modified hydroxyethyl cellulose, hydrophobically modified hydroxyethylcellulose, hydrophobically-modified hydroxypropylcellulose, cationic hydrophobically-modified hydroxypropyl cellulose, cationic carboxymethylhydroxyethylcellulose, and cationic hydroxypropylcellulose.

38. The composition of claim 35, wherein the member is the nonionic, anionic, hydrophobically modified, amphoteric, and cationic polygalactomannan selected from the group consisting of carboxymethyl guar, hydroxypropyl guar, hydrophobically-modified guar, carboxymethyl guar hydroxypropyltrimethylammonium chloride, guar hydroxypropyltrimethylammonium chloride, and hydroxypropyl guar hydroxypropyltrimethylammonium chloride, hydroxybutyl guar, hydroxybutyl guar hydroxypropyltrimethylammonium chloride, hydroxyethyl guar, hydroxyethyl guar hydroxypropyltrimethylammonium chloride, and locust bean.

39. The composition of claim 35, wherein the member is the viscosifying agent that is selected from the group consisting of NaCl, $NH_4Cl$, KCl, and fatty alcohols, fatty acid esters, fatty acid amides, fatty alcohol polyethyleneglycol ethers, sorbitol polyethyleneglycol ethers, polyethyleneoxide fatty acid esters, ethyleneglycol monostearate or distearate, cocamidopropyl betaine, clays, silicas, cellulosic polymers, xanthan, alginates, guar and guar derivatives, carrageenan, Konjac flour, gelatin, dextrin, pectin, starch, and mixtures thereof.

40. The composition of claim 35, wherein the member is the silicone material that is selected from the group consisting of cyclosiloxane, linear siloxane, comb or graft siloxane structure with polyol, amino, quaternary ammonium or other functional groups in the siloxane structure, and mixtures thereof.

41. The composition of claim 40, wherein the member is the other functional groups that are selected from the group consisting of polyethylenoxy and/or polypropylenoxy groups optionally containing $C_6$-$C_{24}$ alkyl groups, substituted or unsubstituted amine groups, thiol groups, alkoxylated groups, hydroxyl groups, acyloxyalkyl groups.

42. The composition of claim 40, wherein the silicone material is selected from the group consisting of polyalkylsiloxanes, polyarylsiloxanes, polyalkylarylsiloxanes, and mixtures thereof.

43. The composition of claim 42, wherein the member is the polyalkylsiloxane that is selected from the group consisting of polydimethylsiloxane, polydimethylsiloxane hydroxylated at the end of the chain, and mixtures thereof.

44. The composition of claim 35, wherein the member is the surfactant that is anionic, cationic, amphoteric, or non-ionic or a mixture thereof.

45. A composition for conditioning surfaces comprising the composition of claim 1, and the surfaces are selected from the group consisting of skin, hair, protein, polyester, cellulose, paper, and textile substrates.

46. The composition of claim 1 is a household care composition that further comprising at least one other active household ingredient.

47. The household care composition of claim 46, wherein the active household ingredient is selected from the group consisting of insect repellent agent, pet deodorizer agent pet shampoo active, industrial grade bar and liquid soap active, dishwashing soap active, all purpose cleaner, disinfecting agent, grass and plant feeding agents, water treatment agent rug and upholstery cleaning active, laundry softener active, laundry detergent active, toilet bowl cleaning agent fabric sizing agent, dust collection agent, antiredeposition agent, textile cleaning agent, softening, antistatic, and lubricating agent.

48. The household care composition of claim 46, wherein the composition also includes at least one additional ingredient selected from the group consisting of colorant, preservative, antioxidant, bleaching agent, activity enhancer, emulsifier, functional polymer, viscosifying agent alcohol, fat or fatty compound, oil, surfactant, fragrance, suspending agent silicone material, and mixtures thereof.

49. The composition of claim 1 is a personal care composition further comprising at least one other active personal care ingredient.

50. The personal care composition of claim 49, wherein the active personal care ingredient is selected from the group consisting of perfumes, skin coolants, emollients, moisturizer, deodorants, antiperspirants actives, moisturizing agents, cleansing agents, sunscreen actives, hair treatment agents, oral care agents, denture adhesive agents, shaving actives, beauty aids, and nail care active.

51. The personal care composition of claim 49, wherein the composition is a product selected from the group consisting of hair care, skin care, sun care, nail care, and oral care.

52. The composition of claim 51, wherein the product is a hair care product comprising a conditioning agent selected from the group consisting of silicone materials, hydrocarbon oils, panthenol and derivatives thereof, pantothenic acid and derivatives thereof, and mixtures thereof.

53. The composition of claim 51, wherein the product is a skin care product comprising a conditioning agent selected from the group of consisting of silicone materials, hydrocarbon oils, panthenol and derivatives thereof, pantothenic acid and derivatives thereof, and mixtures thereof.

54. The composition of claim 53, wherein the skin care product comprises a emollient agent selected from the group of consisting of polyhydric alcohols and hydrocarbons.

55. The composition of claim 51, wherein the product is the hair care product or skin care product that comprises up to 99% by weight based on the total composition of the cationic, oxidized polysaccharide or derivative thereof of claim 1.

56. The personal care composition of claim 49, wherein the composition also includes at least one additional ingredient selected from the group consisting of colorant, preservative, antioxidant, alpha or beta hydroxy acid, activity enhancer, emulsifier, functional polymer, viscosifying agent, alcohol, fat or fatty compound, antimicrobial compound, zinc pyrithione, silicone material, anti-dandruff, hydrocarbon polymer, emollient, oil, surfactant, flavor, fragrance, medicaments, rejuvenating agents, suspending agents, stabilizing biocides, and mixture thereof.

57. The composition of claim 1, further comprising water in an amount of 1 to 99% by weight of the total composition.

58. Personal care or household care composition comprising at least one cationic, oxidized polysaccharide or derivative thereof having a weight average molecular weight with a lower limit of 42030 and an upper limit of 1,000,000, having aldehyde functionality content of at least 0.001 meq/gram of polysaccharide, wherein the personal care or household care composition containing 4.55% by weight of the cationic, oxidized polysaccharide or derivative thereof has a light transmittance of 71.6% at a wavelength of 600 nm in an aqueous solution.

59. Personal care or household care composition comprising at least one cationic, oxidized polysaccharide or derivative thereof having a weight average molecular weight with a lower limit of 42030 and an upper limit of 1,000,000, having aldehyde functionality content of at least 0.001 meq/gram of polysaccharide, wherein the personal care or household care composition containing 7.27% by weight of the cationic, oxidized polysaccharide or derivative thereof has a light transmittance of 62% at a wavelength of 600 nm in an aqueous solution.

60. Personal care or household care composition comprising at least one cationic, oxidized polysaccharide or derivative thereof having a weight average molecular weight with a lower limit of 42030 and an upper limit of 1,000,000, having aldehyde functionality content of at least 0.001 meq/gram of polysaccharide, wherein the personal care or household care composition containing 9.10% by weight of the cationic, oxidized polysaccharide or derivative thereof has a light transmittance of 57.7% at a wavelength of 600 nm in an aqueous solution.

61. Personal care or household care composition comprising at least one cationic, oxidized polysaccharide or derivative thereof having a weight average molecular weight with a lower limit of 42030 and an upper limit of 1,000,000, having aldehyde functionality content of at least 0.001 meq/gram of polysaccharide, wherein the personal care or household care composition containing 13.64% by weight of the cationic, oxidized polysaccharide or derivative thereof has a light transmittance of 43.5% at a wavelength of 600 nm in an aqueous solution.

* * * * *